(12) United States Patent
McTavish et al.

(10) Patent No.: US 11,324,834 B2
(45) Date of Patent: May 10, 2022

(54) INSULIN-LIKE GROWTH FACTOR-CHEMOTHERAPEPUTIC CONJUGATE FOR TREATING MYELODYSPLASTIC SYNDROME

(71) Applicant: IGF Oncology, LLC, Pine Springs, MN (US)

(72) Inventors: Hugh McTavish, Pine Springs, MN (US); Arkadiusz Z. Dudek, Vadnais Heights, MN (US)

(73) Assignee: IGF Oncology, LLC, Pine Springs, MN (US)

( * ) Notice: Subject to any disclaimer, the term of this patent is extended or adjusted under 35 U.S.C. 154(b) by 0 days.

(21) Appl. No.: 16/006,561

(22) Filed: Jun. 12, 2018

(65) Prior Publication Data

US 2018/0333501 A1 Nov. 22, 2018

Related U.S. Application Data

(63) Continuation of application No. PCT/US2018/033747, filed on May 21, 2018.

(60) Provisional application No. 62/509,150, filed on May 21, 2017.

(51) Int. Cl.
| | | |
|---|---|---|
| *A61K 47/64* | (2017.01) | |
| *A61P 35/02* | (2006.01) | |
| *A61K 38/30* | (2006.01) | |
| *A61P 7/00* | (2006.01) | |
| *A61K 31/7068* | (2006.01) | |
| *A61K 31/519* | (2006.01) | |

(52) U.S. Cl.
CPC ...... *A61K 47/6425* (2017.08); *A61K 31/7068* (2013.01); *A61K 38/30* (2013.01); *A61K 47/64* (2017.08); *A61P 7/00* (2018.01); *A61P 35/02* (2018.01); *A61K 31/519* (2013.01)

(58) Field of Classification Search
None
See application file for complete search history.

(56) References Cited

U.S. PATENT DOCUMENTS

| | | | |
|---|---|---|---|
| 4,876,242 A | 10/1989 | Applebaum | |
| 4,975,278 A | 12/1990 | Senter | |
| 5,122,368 A | 6/1992 | Greenfield | |
| 5,444,045 A | 8/1995 | Francis | |
| 5,518,888 A | 5/1996 | Waldman | |
| 5,830,995 A | 11/1998 | Shoyab | |
| 5,869,045 A | 2/1999 | Hellstrom | |
| 5,886,141 A | 3/1999 | Folkman | |
| 7,811,982 B2 | 10/2010 | McTavish | |
| 8,017,102 B2 | 9/2011 | McTavish | |
| 2002/0197261 A1 | 12/2002 | Li | |
| 2003/0092631 A1 | 5/2003 | Deshayes | |
| 2003/0138430 A1 | 7/2003 | Stimmel | |
| 2003/0180937 A1 | 9/2003 | Georgiou | |
| 2004/0023887 A1 | 2/2004 | Pillutla | |
| 2004/0086503 A1 | 5/2004 | Cohen | |
| 2004/0137071 A1 | 7/2004 | Unger | |
| 2004/0142381 A1 | 7/2004 | Hubbard | |
| 2004/0038303 A1 | 12/2004 | Unger | |
| 2004/0248787 A1 | 12/2004 | Naito | |
| 2010/0121036 A1 | 5/2010 | Fischer | |
| 2010/0143340 A1* | 6/2010 | Kolhe | A61K 39/395 424/131.1 |
| 2010/0226884 A1 | 9/2010 | Chang | |
| 2011/0275566 A1 | 11/2011 | Besner | |
| 2013/0323785 A1 | 12/2013 | Sohn | |
| 2015/0196656 A1* | 7/2015 | McTavish | C07K 14/525 514/8.6 |

FOREIGN PATENT DOCUMENTS

| | | |
|---|---|---|
| EP | 0309050 | 3/1989 |
| EP | 0398305 | 11/1990 |
| EP | 1557429 A1 | 7/2005 |
| WO | WO 88/08715 | 11/1988 |
| WO | WO 93/21939 | 11/1993 |
| WO | WO 01/93900 | 12/2001 |
| WO | WO 02/49672 | 6/2002 |
| WO | WO 03/074551 | 9/2003 |
| WO | WO 2014/160956 | 10/2014 |

OTHER PUBLICATIONS

Clinical Trial NCT02045368(Apr. 27, 2017 version) downloaded from ClinicalTrials.gov on Dec. 5, 2019.*
Schanz et al., DOI:10.1200/JCO.2011.35.6394, Journal of Clinical Oncology 30(8):820-829, Mar. 10, 2012, published online Feb. 13, 2012.*
Cook et al., Cancer Metastasis Rev. Jun. 2013 ; 32(0): 63-76. doi:10.1007/s10555-012-9405-5.*
Clinical Trial NCT02045368(Jan. 27, 2015 version) downloaded from ClinicalTrials.gov on Dec. 5, 2019.*
Ayre SG, Garcia y Bellon DP, Garcia DP Jr. 2000. Insulin, chemotherapy, and the mechanisms of malignancy: the design and the demise of cancer, *Medical Hypotheses* 55:330-334.
Abita JP, Gauville C, Balitrand N, Gespach C, Canivet J. 1984. Binding of 125I-insulin to the human histiocytic lymphoma cell line U-937: effect of differentiation with retinoic acid. *Leuk Res.* 8(2):213-21.
Alabaster O, Vonderhaar BK, Shafie SM. 1981. Metabolic modification by insulin enhances methotrexate cytotoxicity in MCF-7 human breast cancer cells. *Eur J Cancer Clin Oncol.* 17(11):1223-8.
Schilsky RL, Bailey BD, Chabner BA. 1981. Characteristics of membrane transport of methotrexate by cultured human breast cancer cells. *Biochem Pharmacol.* 30(12):1537-42.

(Continued)

*Primary Examiner* — Marianne P Allen
(74) *Attorney, Agent, or Firm* — Hugh McTavish

(57) ABSTRACT

Provided are methods of treating myelodysplastic syndrome (MDS), oligoblastic acute myelogenous leukemia (O-AML), or chronic myelomonocytic leukemia (CMML) using 765IGF-MTX and other IGF-receptor-targeted agents, and formulations for delivering 765IGF-MTX and other IGF-receptor-targeted agents to patients. Also provided are pharmaceutical compositions for use in treating MDS, O-AML, and CMML.

9 Claims, 7 Drawing Sheets

Specification includes a Sequence Listing.

(56) References Cited

OTHER PUBLICATIONS

McTavish et al. 2009. Novel insulin-like growth factor-methotrexate covalent conjugate inhibits tumor growth in vivo at lower dosage than methotrexate alone. *Translational Research* 153:275-282.

Daughaday WH, Rotwein P. 1989. Insulin-like growth factors I and II. Peptide, messenger ribonucleic acid and gene structures, serum, and tissue concentrations. *Endocr Rev.* 10(1):68-91.

Stewart CE, Rotwein P. 1996. Growth, differentiation, and survival: multiple physiological functions for insulin-like growth factors. *Physiol Rev.* Oct. 1996;76(4):1005-26.

Yakar S, Wu Y, Setser J, Rosen CJ. 2002. The role of circulating IGF-I: lessons from human and animal models. Endocrine. 19(3):239-48.

Shackney SE, McCormack GW, Cuchural GJ Jr. 1978. Growth rate patterns of solid tumors and their relation to responsiveness to therapy: an analytical review. *Ann. Intern. Med.* 89:107-21.

Poznansky MJ, Singh R, Singh B, Fantus G. 1984. Insulin: carrier potential for enzyme and drug therapy. *Science* 223(4642):1304-6.

Bures L, Bostik J, Motycka K, Spundova M, Rehak L. 1988. The use of protein as a carrier of methotrexate for experimental cancer chemotherapy. III. Human serum albumin-methotrexate derivative, its preparation and basic testing. *Neoplasma* 35:329-42.

Ciftci K, Su J, Trovitch PB. 2003. Growth factors and chemotherapeutic modulation of breast cancer cells. *J Pharm Pharmacol* 55(8):1135-41.

Francis GL, Ross M, Ballard FJ, Milner SJ, Senn C, McNeil KA, Wallace JC, King R, Wells Jr. 1992. Novel recombinant fusion protein analogues of insulin-like growth factor (IGF)-I indicate the relative importance of IGF-binding protein and receptor binding for enhanced biological potency. *J Mol Endocrinol.* 8(3):213-23.

Tomas FM, Knowles SE, Chandler CS, Francis GL, Owens PC, Ballard FJ. 1993. Anabolic effects of insulin-like growth factor-I (IGF-I) and an IGF-I variant in normal female rats. *J Endocrinol.* 137(3):413-21.

Stehle G, Sinn H, Wunder A, Schrenk HH, Schutt S, Maier-Borst W, Heene DL. 1997. The loading rate determines tumor targeting properties of methotrexate-albumin conjugates in rats. *Anticancer Drugs* 8(7):677-85.

Grothey, A. et al. 1999. The role of unsulin-like growth factor I and its receptor in cell growth, transformation, apoptosis, and chemoresistance in solid tumors. *J. Cancer Res. Clin. Oncol.* 125:166-173.

Carlsson et al.. 1978. Biochem J. 173:723-727.

Laajoki et al. 2000. J. Biol. Chem. 275:1009-15.

Laajoki et al. 1997. FEBS Lett. 420:97-102.

Allen et al. Ligand-targeted therapeutics in anticancer therapy. 2002. Nature Reviews Cancer 2:750-763.

Wang et al. 2002. Insulin-like growth factor receptor-1 as an anti-cancer target: blocking transformation and inducing apoptosis. *Current Cancer Drug Targets* 2:191-207.

Bohula et al. 2003. Targeting the type-1 insulin-like growth factor receptor as anti-cancer treatment. *Anti-cancer Drugs* 14:669-682.

Akhlynina et al. 1997. J. Biol. Chem. 272:20328-31.

Leckett et al. 1992. Cytotechnology 10:125-136.

Satyamoorthy, K. et al. 2001. Insulin-like growth factor-1 induces survival and growth of biologically early melanoma cells . . . *Cancer Res.* 61:7138.

Molhoj et al. Nature Biotechnology, 22(12): 1502, Dec. 2014.

Wang, R-F et al., (1995) Mammalian cell/vaccinia virus expression . . . Gene 153:197-202.

Okana, K. et al., (1990) Functional expression of human leukocyte elastase . . . Biochem. Biophys. Res. Comm. 167:1326-1332.

Kreitman, R.J. et al. (1992) Targeting growth factor receptors with fusion toxins. International Journal of Immunopharmacology 14:465-472.

Guo et al. (2004) Proc. Natl. Acad Sci. USA 101(25):9205-0210.

Alkhateeb HB, Patnaik MM, Al-Kali A, Zblewski DL, Wallerich S, McTavish H, Dudek AZ. Phase 1b Study of IGF-Methotrexate Conjugate in the Treatment of High-grade Myelodysplastic Syndromes. *Anticancer Res.* Jul. 2020;40(7):3883-3888. doi: 10.21873/anticanres.14378.

He Q, Chang CK, Xu F, Zhang QX, Shi WH and Li X: Purification of bone marrow clonal cells from patients with myelodysplastic syndrome via IGF-IR. *PLoS One* 10(10): e0140372, 2015. PMID: 26469401. DOI: 10.1371/journal.pone.0140372.

\* cited by examiner

INSULIN-LIKE GROWTH FACTOR-CHEMOTHERAPEPUTIC CONJUGATE FOR TREATING MYELODYSPLASTIC SYNDROME

A sequence listing as an ASCII text file with the file name 102-009US1-seq_ST25.txt, size 10,000 bytes, created on Jun. 12, 2018, is submitted with this patent application and is hereby incorporated by reference.

BACKGROUND

Myelodysplastic syndrome (MDS) is a hematopoietic disorder derived from an abnormal multipotent progenitor cell, characterized by ineffective hematopoiesis, bone marrow failure, peripheral blood cytopenias, and reduced survival. It includes chronic myelomonocytic leukemia (CMML) as a subtype of MDS. And it often progresses to oligoblastic acute myeloid leukemia (O-AML). MDS, CMML, and O-AML may be considered types of myeloproliferative disorders. CMML and O-AML may also be considered subtypes of MDS diseases closely related to MDS. [Schanz J, Tüchler H, Solé F, et al. New comprehensive cytogenetic scoring system for primary myelodysplastic syndromes (MDS) and oligoblastic acute myeloid leukemia after MDS derived from an international database merge. *J Clin Oncol* 2012; 30:820-829. http://www.clevelandclinicmeded.com/medicalpubs/diseasemanagement/hematology-oncology/myelodysplastic-syndromes/].

Only three drugs are approved for treatment of MDS in the United States. The primary two are the demethylating agents azacitidine (5-AZA, VIDAZA), and decitabine (DACOGEN). These hypomethylating agents purportedly work by reactivating tumor suppressor genes and through direct cytotoxic mechanisms, and may induce hematopoietic progenitor cell differentiation. In a recent phase III trial in higher-risk patients, responses occurred in approximately 50% of patients, and survival was doubled at 2 years of follow-up in patients receiving azacitidine, compared to those treated with conventional care, including best supportive care or chemotherapy. Decitabine has been investigated in a multicenter phase III study, in which responses were achieved in 30% of patients, with a complete and partial remission rate in 17%, though no overall survival advantage has been demonstrated compared to best supportive care. Lenalidomide (REVLIMID), related to thalidomide, is also approved for MDS and has shown efficacy in some but not all types of MDS.

Standard chemotherapy drugs that interfere in some way with DNA replication are not generally used in MDS because they reduce blood cell counts—cause cytopenia—and MDS patients already have cytopenia as a consequence of their disease and cannot tolerate further decreases in blood cell counts. Lenalidomide also has the side effect of causing cytopenia, limiting its utility in MDS.

The existing drugs for MDS, O-AML, and CMML are insufficiently effective. Life expectancy at diagnosis with MDS remains at 4-85 months, with a median of about 24 months [Bennett J M, Catovsky D, Daniel M T, et al. Proposals for the classification of the myelodysplastic syndromes. *Br J Haematol* 1982; 51:189-199. http://www.clevelandclinicmeded.com/medicalpubs/diseasemanagement/hematology-oncology/myelodysplastic-syndromes/]. New drugs and therapies for MDS, O-AML, and CMML are needed.

SUMMARY

We describe here a conjugate (IGF-MTX) of insulin like growth factor-1 (IGF-1 or IGF), or a variant of IGF such as 765IGF, covalently attached to methotrexate (MTX). The conjugate, like methotrexate, is cytotoxic to cancer cells in vitro. The IGF-MTX conjugate, like MTX, inhibits dihydrofolate reductase. The IGF-MTX conjugate has a higher IC50 (50% inhibitor concentration) for inhibiting the growth of cancer cells in vitro than free MTX. But it is more than 6-fold more effective than MTX in inhibiting tumor growth in vivo in a mouse model. That is, IGF-MTX is more effective than MTX even at a 6-fold lower dose in terms of moles of MTX groups dosed per kg.

We now show that in a human clinical trial 765IGF-MTX was effective in delaying tumor growth in some solid tumor patients at a surprisingly low dose of 0.2 microEq per kg. One recurrent Hodgkin's lymphoma patient was also found to be cancer free after weekly treatment with 0.2 microEq/kg of 765IGF-MTX. No dose limiting toxicity was seen in humans in this clinical trial at up to 0.8 microEq/kg. No cytopenia at all was seen in the trial at any dose, including the highest dose tested of 0.8 microEq/kg. In contrast, cytopenia is universal with treatment with methotrexate and is probably the most serious common adverse event seen with methotrexate.

In a 5-week repeat dose study in dogs, with weekly dosing of 0.5, 2.0, and 4.0 microEq/kg of 765IGF-MTX, a slight reduction of erythrocyte mass was seen, although not to levels below the normal range, but no reduction of lymphocytes or neutrophils was seen. In a repeat-dose study in rats dosed weekly for 6 weeks at 0.5, 5, or 8 microEq/kg, no cytopenia was seen at 0.5 microEq/kg, and at 5 microEq/kg there was only a marginal decrease in erythrocyte mass and white blood cells, which reverted to normal after a 3-week recovery period.

The lack of cytopenia with IGF-MTX in humans and in animal toxicology studies makes IGF-MTX attractive for treating leukemias, particularly myeloid leukemias, including acute myeloid leukemia (AML), because cytopenia is a consequence of these diseases. The lack of cytopenia with IGF-MTX in humans and animal toxicology makes it especially attractive for treating myelodysplastic syndrome (MDS) (including the closely related diseases oligoblastic acute myeloid leukemia (O-AML) and chronic myelomonocytic leukemia (CMML)), which is characterized by growth of a myeloid clone in the bone marrow, which crowds out production of other blood cells, resulting in strong cytopenia. The patients become dependent on blood transfusions.

We show here that an MDS cell line and three AML cell lines are all sensitive to 765IGF-MTX in vitro at about the same concentrations as MCF7, which is also sensitive to IGF-MTX in vivo. We also show that the MDS cell line expresses the type 1 IGF membrane receptor (IGF-1R) at a high level similar to MCF7. This suggests that MDS in humans will be sensitive to IGF-MTX and that MDS patients can be treated with IGF-MTX at doses that are effective but cause no cytopenia.

Accordingly, one embodiment of the invention provides a method of treating a patient for oligoblastic acute myelogenous leukemia (O-AML) or myelodysplastic syndrome (MDS) or chronic myelomonocytic leukemia (CMML) comprising: administering to a patient in recognized need of treatment for O-AML, MDS, or CMML an agent comprising: an insulin-like growth factor type 1 receptor (IGF-1R) ligand conjugated to an anti-cancer chemotherapy drug. O-AML and MDS are recognized as very similar diseases to MDS.

Another embodiment provides a method of treating a patient for acute myeloid leukemia (AML), chronic myeloid leukemia (CML), O-AML, CMML, or MDS comprising:

administering to a patient in recognized need of treatment for AML, CML, O-AML, CMML, or MDS (a) a hypomethylating agent (e.g., azacitidine or decitabine) and (b) an agent comprising: an insulin-like growth factor type 1 receptor (IGF-1R) ligand conjugated to methotrexate; wherein the IGF-1R ligand is insulin-like growth factor 1 (IGF-1) or a variant thereof or insulin.

It has been found that 765IGF-MTX, insulin-MTX, and longR3IGF-MTX each tend to have low solubility in phosphate buffered saline, or any neutral pH solution containing salt, for instance over about 50 mM NaCl. Accordingly, 765IGF-MTX is currently stored as a 4 mEq/L solution in 10 mM HCl. For infusion into patients, it is diluted into 250 ml of 5% dextrose or 10% dextrose in water. IGF-MTX causes hypoglycemia, so delivering it as an infusion in 5% dextrose has the benefit of administering dextrose to counteract the expected mild hypoglycemia. And 765IGF-MTX is completely soluble in water with any concentration of dextrose, whereas it tends to precipitate in about 150 mM NaCl at neutral pH.

Accordingly, another embodiment of the invention provides a pharmaceutical composition that is a solution for infusion comprising: (a) an agent consisting of a covalent conjugate an IGF-1R ligand covalently conjugated to methotrexate, wherein the IGF-1R ligand is insulin-like growth factor 1 (IGF-1) or a variant thereof or insulin; dissolved in (b) 100 ml to 1 liter of 5% to 10% (w/v) dextrose in water, wherein the composition does not comprise more than 5 mM NaCl or more than 2 mM phosphate; wherein the solution is in an infusion bag and has a volume of 100 ml to 1 liter.

Another embodiment provides a method of administering an agent consisting of a covalent conjugate an IGF-1R ligand covalently conjugated to methotrexate, wherein the IGF-1R ligand is insulin-like growth factor 1 (IGF-1) or a variant thereof or insulin; the method comprising: diluting the agent into a diluent consisting essentially of a volume of 100 ml to 1 liter of 5% to 10% dextrose (w/v) in water to make a solution of the agent in the diluent; and infusing the solution into a patient. Preferably, the infusion occurs over a time of 30 minutes to 2 hours.

Another embodiment provides a composition comprising: an agent comprising: an insulin-like growth factor type 1 receptor (IGF-1R) ligand conjugated to an anti-cancer chemotherapy drug, for use in a method of treating oligoblastic acute myelogenous leukemia (O-AML) or myelodysplastic syndrome (MDS) or chronic myelomonocytic leukemia (CMML).

Another embodiment provides a device comprising: (a) an infusion bag capable of holding a maximum volume of 100 ml to 2 liters, filled with (b) a solution of 5% or 10% (w/v) dextrose and dissolved in the solution (c) an agent consisting of a covalent conjugate an IGF-1R ligand covalently conjugated to methotrexate, wherein the IGF-1R ligand is insulin-like growth factor 1 (IGF-1) or a variant thereof or insulin, the solution having a volume of 100 ml to 1 liter (more preferably 100 ml to 500 ml, 150 ml to 500 ml, or about 250 ml).

DETAILED DESCRIPTION

Definitions

Figure 1:
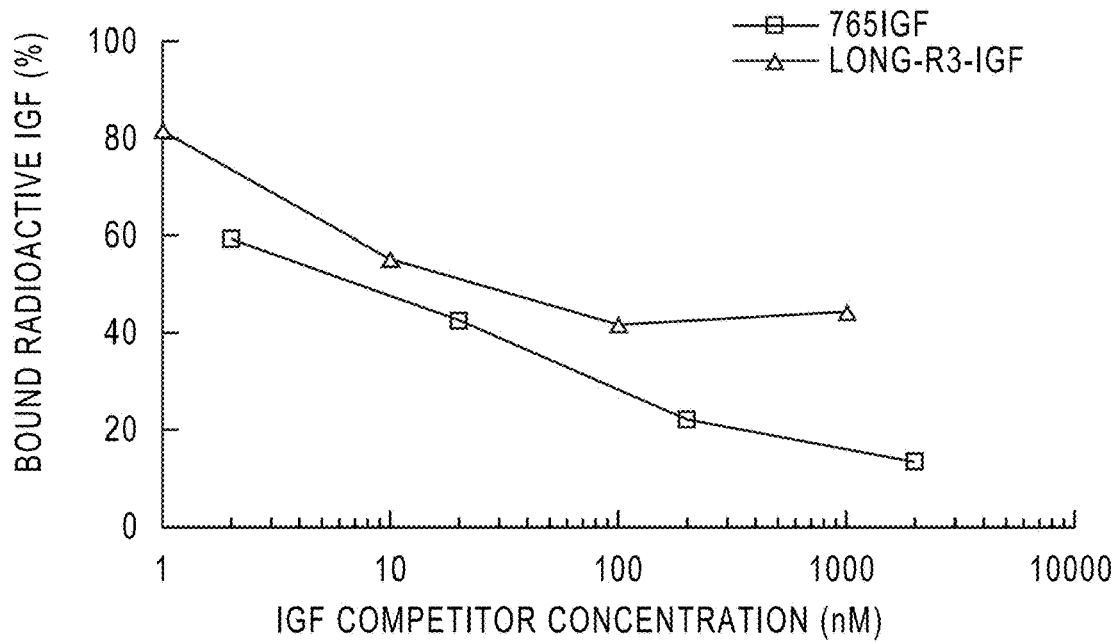
FIG. 1. Competition binding assay of 765IGF and longR3-IGF to IGF1R on MCF7 cells versus I-125-labeled IGF1.

The term "anti-cancer chemotherapeutic drug or agent" refers to a synthetic, biological, or semi-synthetic compound that is not an enzyme and that kills cancer cells or inhibits the growth of cancer cells while having less effect on non-cancerous cells. It does not include antibodies or molecules naturally made by mammals, such as growth factors and cytokines.

The term "treating cancer" includes, e.g., preventing metastasis, inhibiting growth of a cancer, stopping the growth of cancer, or killing cells of a cancer.

The term "binding affinity" of a ligand for a particular receptor refers to the association constant $K_A$ (the inverse of the dissociation constant $K_D$) or to experimentally determined approximations thereof.

The term "anti-metabolite" refers to an anti-cancer chemotherapeutic agent that bears a structural similarity to a naturally occurring substance, interacts with enzymes as an inhibitor or a substrate, and interferes with cellular processes. Examples include methotrexate, fluorouracil, floxuridine, fludarabine, mercaptopurine, thioguanine, cytarabine, azacitidine, cladribine, and pentostatin.

The "IGF-1 receptor" is also known in the literature as the type 1 IGF receptor and is abbreviated herein as IGF-1R.

"Containing" as used herein is open-ended; i.e., it allows the inclusion of other unnamed elements and has the same meaning as "comprising."

The term "leader sequence" as used herein refers to an amino acid sequence a the N-terminus of a protein. It is not cleaved off after synthesis of the protein but is part of the mature protein.

Description:

One embodiment of the invention provides a method of treating a patient for oligoblastic acute myelogenous leukemia (O-AML) or myelodysplastic syndrome (MDS) or chronic myelomonocytic leukemia (CMML) comprising: administering to a patient in recognized need of treatment for O-AML, MDS, or CMML an agent comprising: an insulin-like growth factor type 1 receptor (IGF-1R) ligand conjugated to an anti-cancer chemotherapy drug. O-AML and CMML are recognized as very similar diseases to MDS.

Another embodiment provides a method of treating a patient for acute myeloid leukemia (AML), or chronic myeloid leukemia (CML), or O-AML, or CMML, or MDS comprising: administering to a patient in recognized need of treatment for AML, CML, O-AML, CMML, or MDS (a) a hypomethylating agent (e.g., azacitidine or decitabine) and (b) an agent comprising: an insulin-like growth factor type 1 receptor (IGF-1R) ligand conjugated to methotrexate; wherein the IGF-1R ligand is insulin-like growth factor 1 (IGF-1) or a variant thereof or insulin. Typically, the hypomethylating agent and the agent comprising an IGF-1R ligand conjugated to methotrexate are administered on the same day.

It has been found that 765IGF-MTX, insulin-MTX, and longR3IGF-MTX each tend to have low solubility in phosphate buffered saline, or any neutral pH solution containing salt, for instance over about 50 mM NaCl. Accordingly, 765IGF-MTX is currently stored as a 4 mEq/L solution in 10 mM HCl. For infusion into patients, it is diluted into 250 ml of 5% dextrose or 10% dextrose in water. IGF-MTX causes hypoglycemia, so delivering it as an infusion in 5% dextrose has the benefit of administering dextrose to counteract the expected mild hypoglycemia. And 765IGF-MTX is completely soluble in water with any concentration of dextrose, whereas it tends to precipitate in about 150 mM NaCl at neutral pH.

Accordingly, another embodiment of the invention provides a pharmaceutical composition that is a solution for infusion comprising: (a) an agent consisting of a covalent conjugate an IGF-1R ligand covalently conjugated to methotrexate, wherein the IGF-1R ligand is insulin-like growth factor 1 (IGF-1) or a variant thereof or insulin; dissolved in (b) 100 ml to 1 liter of 5% to 10% (w/v) dextrose in water, wherein the composition does not comprise more than 5 mM NaCl or more than 2 mM phosphate; wherein the solution is in an infusion bag and has a volume of 100 ml to 1 liter.

Another embodiment provides a method of administering an agent consisting of a covalent conjugate an IGF-1R ligand covalently conjugated to methotrexate, wherein the IGF-1R ligand is insulin-like growth factor 1 (IGF-1) or a variant thereof or insulin; the method comprising: diluting the agent into a diluent consisting essentially of a volume of 100 ml to 1 liter of 5% to 10% dextrose (w/v) in water to make a solution of the agent in the diluent; and infusing the solution into a patient. Preferably, the infusion occurs over a time of 30 minutes to 2 hours.

The IGF-1R ligand may be an antibody that specifically binds to IGF-1R. In other embodiments it is insulin or IGF-1 (SEQ ID NO:3) or a variant of IGF-1. A preferred specific variant is 765IGF (SEQ ID NO:2).

In specific embodiments, the anti-cancer chemotherapy drug is methotrexate, chlorambucil, or bendamustine. In a specific embodiment it is methotrexate.

In a specific embodiment, the chemotherapy drug is a small molecule (molecular weight smaller than 2000 daltons) that is not a protein or peptide and that contains a free carboxyl group. These can be conjugated to a protein IGF-1R ligand by reaction with EDC to conjugate the carboxyl to amino groups of the protein.

A specific embodiment of the methods of treating patients described herein involve administration of an IGF-1R ligand conjugated to methotrexate, preferably 765IGF-MTX, at a dose of 0.1 to 2.5 microEq per kg patient body weight. In other embodiments the dose is 0.2 to 2.5, 0.4 to 2.5, or 0.4 to 1.6, about 0.2, about 0.4, about 0.8, or about 1.6, or about 2.5 microEq/kg. Dosing is preferably once weekly, but may be twice weekly or once per 2 weeks or once per 3 weeks. In one embodiment, dosing is once per week for 3 weeks, followed by one week off, in a 28-day cycle. Dosing is preferably by intraveneous infusion. In one embodiment, the conjugate (an IGF-1R ligand conjugated to an anti-cancer chemotherapy drug) is administered by intravenous infusion in 5% to 10% dextrose in a volume of 100 ml to 1 liter (more preferably about 200 ml to about 500 ml, and in other embodiments 100 to 500 ml, 150 to 500 ml, 200 to 500 ml, or about 250 ml, or about 500 ml).

The IGF-1R ligand in some embodiments is covalently attached to the chemotherapy drug. In other embodiments, it may be conjugated by non-covalent attachment, for instance by embedding the chemotherapy drug and IGF-1R ligand together in nanoparticles, similarly to the way ABRAXANE is a nanoparticle of paclitaxel associated with albumin.

In specific embodiments, the IGF-1R ligand is insulin-like growth factor-1 (IGF-1), or a variant thereof, or insulin. The variants of IGF-1 preferably have reduced binding affinity for soluble IGF binding proteins as compared to native IGF-1. Soluble IGF binding proteins are soluble proteins in the blood that binding to IGF-1, as opposed to the IGF-1R membrane receptor that is a membrane protein through which IGF-1 exerts its biological action. As much as 99% of IGF-1 in vivo is bound to the soluble IGF binding proteins, and when it is bound to the soluble IGF binding proteins it is unavailable for binding to IGF-1R. Below specific variants of IGF-1 that have reduced binding affinity for the soluble IGF binding proteins are described, as well as an assay for determining binding affinity to the soluble IGF binding proteins.

We have expressed in *E. coli*, from a recombinant vector with expression controlled by a T7 promoter and induced with IPTG, a fusion protein having the sequence of SEQ ID NO:2. This protein has the sequence at its N-terminus of SEQ ID NO:1, which provides a polyhis tag for purification and several additional lysine residues. The C-terminal of the protein is residues 19-88 and corresponds to R3-IGF, which is human wild type IGF-1 sequence with an arginine at position 21 of SEQ ID NO:2 that replaces the native glutamic acid at position 3 of wild-type IGF-1 (SEQ ID NO:3).

R3-IGF (SEQ ID NO:6) is a variant IGF-1, as discussed below.

765IGF (SEQ ID NO:2) comprising SEQ ID NO: 1 as an N-terminal sequence followed by R3-IGF expressed at a high yield and purified at a higher yield than other IGF fusion protein constructs comprising different leader sequences. It was more stable to storage than IGF132, another variant of IGF-1. It also refolded with almost 100% yield of active form, and it displaced more wild-type IGF-1 from its receptor on MCF7 cells than did long-R3-IGF, another variant of IGF-1.

The SEQ ID NO:1 leader also provides five lysine residues. A 765IGF-methotrexate conjugate was prepared by covalently attaching methotrexate through one of its carboxyl groups by amide bond to amino groups on 765IGF. 765IGF has nine amino groups, including eight lysine side chains (five of these in the SEQ ID NO:1 leader) and the amino terminal alpha-amino group. The 765IGF-MTX had an average of about 8 methotrexate groups attached per IGF monomer. Conjugates to longR3-IGF and IGF132 had fewer methotrexate groups per IGF monomer. So this was another advantage of the SEQ ID NO:1 leader.

R3-IGF is a variant IGF-1 in a fusion protein with SEQ ID NO:1 in SEQ ID NO:2. It is a variant that activates the IGF receptor (IGF-1R) but has reduced binding affinity for the soluble IGF binding proteins (as compared to wild-type IGF-1) (Francis, G. L., et al. 1992, *J. Mol. Endocrinol.* 8:213-223; Tomas, F. M. et al., 1993, *J. Endocrinol.* 137: 413-421). Soluble IGF binding proteins are natural serum proteins that bind to IGF-1, holding it in circulation and extending its biological half-life. But when IGF-1 is bound to the IGF binding proteins it cannot bind to the membrane IGF receptor (IGF-1R). (Clemons, D. R., 1998, Mol. Cell. Endocrinol. 140:19-24.) For that reason, variants of IGF-1 that have reduced binding to the soluble IGF binding proteins are more active in vivo than wild-type IGF-1 and more rapidly target the IGF receptor.

Binding affinity for IGF binding proteins can be tested with rat L6-myoblast-conditioned medium. The medium from growth of rat L6 myoblasts (0.2 ml) is mixed with 8,000 cpm $^{125}$I-IGF-1 (approximately 0.05 uCi) in 0.3 ml final volume of 50 mM sodium phosphate, pH 6.5, 0.25% bovine albumin and test competitor (wild type IGF-1 or an IGF variant) at 0.1 nM to 1 uM final concentration. After incubation 90 minutes at room temperature, to separate bound and free tracer an ice cold rapidly stirred suspension of charcoal at 5 mg/ml in assay buffer containing 0.2 mg/ml protamine sulfate is added to the sample, and after 8 minutes on ice, the mixture is centrifuged 20 minutes at 5,000×g. Radioactivity in the supernatant is counted in a gamma counter. The binding affinity of a variant can be compared to that of wild-type IGF to determine whether a variant has reduced binding affinity for the soluble IGF binding proteins.

Some specific variants of IGF-1 with reduced binding affinity to the soluble IGF binding proteins include IGF132 (SEQ ID NO:4) (disclosed in U.S. Pat. No. 4,876,242), LONG-R3-IGF (SEQ ID NO:5), R3-IGF (SEQ ID NO:6), and des(1-3)IGF1 (SEQ ID NO:7), which lacks the first three residues of wild-type IGF-1. (LongR3-IGF, R3-IGF, and des(1-3)IGF1, are described in Francis, G. L., et al. 1992, *J. Mol. Endocrinol.* 8:213-223; Tomas, F. M. et al., 1993, *J. Endocrinol.* 137:413-421). Thus, in particular embodiments, the polypeptide that is a variant IGF-1 with reduced binding to the soluble IGF-1 binding proteins comprises any one of SEQ ID NOS:4-7.

The IGF receptor may be targeted in cancer with conjugates comprising (a) an anti-cancer chemotherapeutic agent covalently coupled to (b) an IGF receptor ligand such as IGF-1 or the IGF variants described herein. Because insulin has affinity for IGF-1R, the IGF-1R ligand may also be insulin.

Preferably, the IGF-1 receptor ligand with reduced affinity for soluble IGF-1 binding proteins has at least 5-fold, more preferably at least 10-fold, more preferably still at least 100-fold lower binding affinity for soluble IGF-1 binding proteins than wild-type IGF-1. Binding affinity for the soluble IGF-1 binding proteins can be measured by a competition binding assay against labeled IGF-1 (e.g., $^{125}$I IGF-1), using a mixture of purified IGF-1 binding proteins or rat L6 myoblast-conditioned medium (a naturally produced mixture of IGF-1 binding proteins), as described in Francis, G. L., et al. (1992, *J. Mol. Endocrinol.* 8:213-223); Szabo, L. et al. (1988, *Biochem. Biophys. Res. Commun.* 151:207-214); and Martin, J. L. et al. (1986, *J. Biol. Chem.* 261:8754-8760). Preferably, the variant IGF-1 has an IC$_{50}$ in a competition binding assay against labeled wild-type IGF-1 for binding to soluble IGF-1 binding proteins in L6 myoblast-conditioned medium of greater than 10 nM, more preferably greater than 100 nM.

Preferably, the IGF-1R ligand, such as the variant IGF-1 variant with reduced affinity for soluble IGF-1 binding proteins, has affinity for the IGF-1 receptor that is close to wild-type IGF-1 (e.g., less than 30-fold greater than wild-type IGF-1, more preferably less than 10-fold greater than wild-type IGF-1). In specific embodiments, the variant IGF-1 has an K$_D$ in a competition binding assay against labeled wild-type IGF-1 for binding to IGF-1 receptors (e.g., on MCF-7 cells) of less than 50 nM, more preferably less than 10 nM, more preferably still less than 5 nM, more preferably still less than 3 nM). This assay is described in Ross, M. et al. (1989, *Biochem. J.* 258:267-272) and Francis, G. L., et al. (1992, *J. Mol. Endocrinol.* 8:213-223), and in Example 4 herein.

In a specific embodiment of the invention the IGF-1 variant comprises IGF-1 (SEQ ID NO:3) or comprises a segment at least 90% identical to any one of SEQ ID NOS:3 and 4.

In specific embodiments, the anti-cancer chemotherapeutic drug may be one with a free carboxyl group, such as methotrexate, chlorambucil, or bendamustine.

In particular embodiments, the chemotherapeutic agent conjugated to the IGF-1R ligand is mechlorethamine, cyclophosphamide, ifosfamide, melphalan, chlorambucil, thiotepa, hexamethylmelamine, busulfan, carmustine, lomustine, semustine, streptozocin, decarbazine, vincristine, vinblastine, etoposide, teniposide, paclitaxel, docetaxel, daunorubicin, idarubicin, doxorubicin, epirubicin, dactinomycin, plicamycin, mitomycin C, bleomycin, mitoxantrone, methotrexate, fluorouracil, floxuridine, fludarabine, mercaptopurine, thioguanine, cytarabine, azacitidine, cladribine, pentostatin, cisplatin, carboplatin, mitotane, procarbazine, or amsacrine.

In specific embodiments of the methods, the IGF-1R ligand is not IGF-1 (SEQ ID NO:3) and is or comprises 765IGF (SEQ ID NO:2), IGF132 (SEQ ID NO:4), long-R3-IGF (SEQ ID NO:5), R3-IGF (SEQ ID NO:6), or des(1-3) IGF1 (SEQ ID NO:7), or a variant at least 90% identical to IGF-1.

In other embodiments, the IGF-1R ligand is an antibody against IGF-1R.

In specific embodiments where the IGF-1R ligand is conjugated to methotrexate, the method comprises dosing the patient with the agent at a dose of 0.1 to 2.5 microEq/kg, 0.1 to 2.5, 0.4 to 2.5, 0.4 to 1.6, about 0.2, about 0.4, about 0.8, about 1.6, or about 2.5 microEq/kg. A microEq is a micromole of methotrexate groups (conjugated to the ligand).

In the methods comprising administering a hypomethylating agent, the hypomethylating agent is preferably azacitidine or decitabine, more preferably azacitidine.

One embodiment provides a pharmaceutical composition that is a solution for infusion comprising: (a) an agent consisting of a covalent conjugate an IGF-1R ligand covalently conjugated to methotrexate, wherein the IGF-1R ligand is insulin-like growth factor 1 (IGF-1) or a variant thereof or insulin; dissolved in (b) 100 ml to 1 liter of 5% to 10% (w/v) dextrose in water, wherein the solution does not comprise more than 5 mM NaCl or more than 2 mM phosphate; wherein the solution is in an infusion bag and has a volume of 100 ml to 1 liter.

In more specific embodiments, the solution has a volume of 100 ml to 500 ml, 150 ml to 500 ml, 200 ml to 500 ml, or about 250 ml, or about 500 ml.

In a specific embodiment, the agent is 765IGF-MTX.

In more specific embodiments, the composition comprises less than 1 mM NaCl and less than 1 mM phosphate.

Another embodiment provides a method of administering an agent consisting of a covalent conjugate an IGF-1R ligand covalently conjugated to methotrexate, wherein the IGF-1R ligand is insulin-like growth factor 1 (IGF-1) or a variant thereof or insulin; the method comprising: diluting the agent into a diluent consisting essentially of a volume of 100 ml to 1 liter of 5% to 10% dextrose (w/v) in water to make a solution of the agent in the diluent; and infusing the solution into a patient.

In specific embodiment, the step of infusing the solution into a patient occurs over a time of 20 minutes to 2.5 hours, or over 30 minutes to 2 hours, or over 45 minutes to 1.5 hours, or over 1 to 2 hours.

Another embodiment provides a composition comprising: an agent comprising: an insulin-like growth factor type 1 receptor (IGF-1R) ligand conjugated to an anti-cancer chemotherapy drug, for use in a method of treating oligoblastic acute myelogenous leukemia (O-AML) or myelodysplastic syndrome (MDS) or chronic myelomonocytic leukemia (CMML) or acute myeloid leukemia (AML) or chromic myeloid leukemia (CML).

Another embodiment provides a device comprising: (a) an infusion bag capable of holding a maximum volume of 100 ml to 2 liters, filled with (b) a solution of 5% or 10% (w/v) dextrose and dissolved in the solution (c) an agent consisting of a covalent conjugate an IGF-1R ligand covalently conjugated to methotrexate, wherein the IGF-1R ligand is insulin-like growth factor 1 (IGF-1) or a variant thereof or insulin, the solution having a volume of 100 ml to 1 liter (more preferably 100 ml to 500 ml, 150 ml to 500 ml, or about 250 ml).

The device may further comprise (d) tubing connected to the infusion bag, and (e) a hypodermic needle connected to the tubing.

In one embodiment, the agent is 765IGF-MTX.

In one embodiment of the device the solution comprises at least 10 microEq of the agent and no more than 250 microEq of the agent.

In specific embodiments of the device the solution comprises no more than 5 mM NaCl (preferably no more than 1 mM NaCl) and no more than 2 mM phosphate (preferably no more than 1 mM phosphate).

In specific embodiments of the device, the solution comprises no more than 5 mM NaCl (preferably no more than 1 mM NaCl, more preferably no NaCl).

Guidelines for Coupling Anti-Cancer Chemotherapeutic Agents to Receptor Ligands

The natural ligands to the insulin and IGF-1 receptors are proteins, namely insulin, IGF-1, and IGF-2. Chemotherapeutic agents are typically coupled to proteins through the reactive groups present on proteins. These include the N-terminal alpha-amino group, the C-terminal alpha-carboxyl group, the side-chain amino group of lysine, the side-chain carboxyl groups of aspartic acid and glutamic acid, the side chain thiol of cysteine, and the side chain of arginine. Other reactive side chains found on proteins are the side-chain hydroxyl of serine and threonine, the hydroxyaryl of tyrosine, the imidazole of histidine, and the methionine side chain.

Many of the same reactive groups are found on chemotherapeutic agents and on non-proteinaceous ligands of the insulin and IGF-1 receptors. Thus, many of the principles of modification and cross-linking of proteins discussed herein also apply to modification and cross-linking of chemotherapeutic agents and non-proteinaceous ligands.

The chemistry and principles of protein conjugation and cross-linking are described in Wong, Shan S., *Chemistry of Protein Conjugation and Cross-Linking,* 1991, CRC Press, Boca Raton, Fla. Other sources for information on this chemistry include the Pierce Biochemistry catalog; and Greene, T. W., and Wutz, P. G. M., *Protecting Groups in Organic Synthesis*, second edition 1991, John Wiley & Sons, Inc., New York, and references cited therein.

The strongest nucleophile of amino acid side chains is the thiol of reduced cysteine side chains. The thiol reacts with most protein modifying reagents. Alpha-haloacetamides and maleimides are considered to react specifically with cysteine residues, particularly at pH 7.0 and below. Thiols also react by disulfide interchange with disulfide reagents.

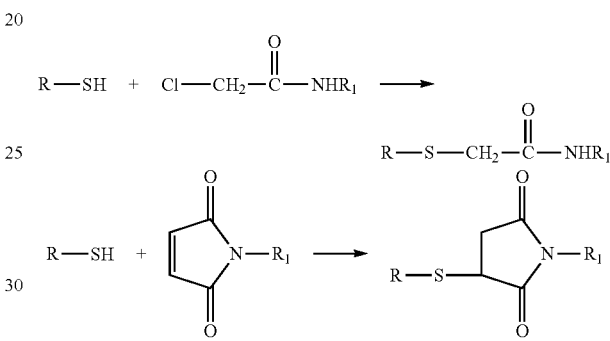

Amino groups are the next-strongest nucleophiles found on proteins. Aldehydes react with amino groups to form Schiff bases. The Schiff bases are hydrolyzable, which can be an advantage in the present invention. With uptake into cancer cells of a ligand-chemotherapeutic agent conjugate, in some cases it is necessary that the chemotherapeutic agent is cleaved from the conjugate for it to be active. This is better accomplished if the chemotherapeutic agent is linked to the ligand by a cleavable linkage, such as a hydrolyzable linkage. Cleavable linkages can be cleaved spontaneously or by enzymes in the cell. For instance, amide bonds are cleaved by certain enzymes, including proteases. A Schiff base linkage spontaneously hydrolyzes at an appreciable rate. A disulfide linkage is expected to be reductively cleaved in the intracellular reducing environment of a cancer cell.

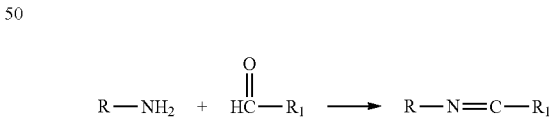

The Schiff base formed by reaction of an amino group with an aldehyde can be stabilized by reduction with, for instance, sodium borohydride or pyridine borane. Pyridine borane has the advantage of not reducing disulfides, which are found in insulin, IGF-1, and IGF-2 and are essential for the structure of those proteins.

Sugars or other moieties having hydroxyl groups on adjacent carbons, which are found in some chemotherapeutic agents, can be modified to react with amino groups by oxidizing the sugars with, for instance, periodate. This cleaves between the carbons and produces a dialdehyde. The aldehyde groups will react with amino groups.

A dialdehyde, such as glutaraldehyde, will cross-link two molecules having amino groups.

Other amino reagents include activated carbonyls, such as N-hydroxysuccinimide esters, p-nitrophenyl esters, or acid anhydrides (e.g., succinic anhydride).

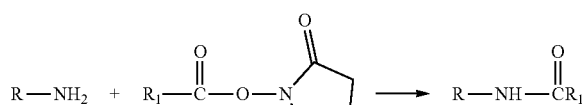

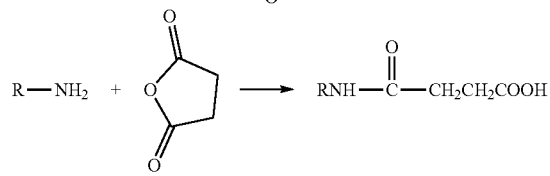

Amino groups also react with sulfonyl halides and aryl halides (e.g, 2,4-dinitrofluorobenzene).

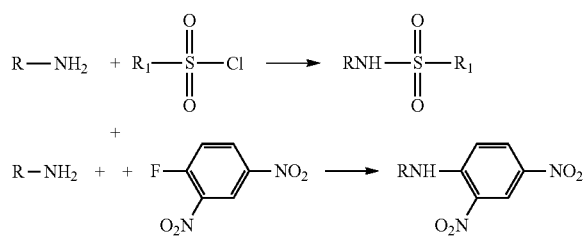

Amino groups also react with isocyanates and isothiocyanates to form urea or thiourea derivatives.

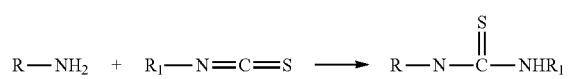

Imidoesters are the most specific acylating agents for amino groups. Imidoesters react specifically with amines to from imidoamides at pHs between about 7 and 10. This reaction has the advantage of maintaining charge stability by generating a positively charged group, the imidoamide, at the former amino group. Imidoamides also slowly hydrolyze at pHs above neutrality, which can also be an advantage in that the hydrolysis can release free chemotherapeutic agent in the cancer cell.

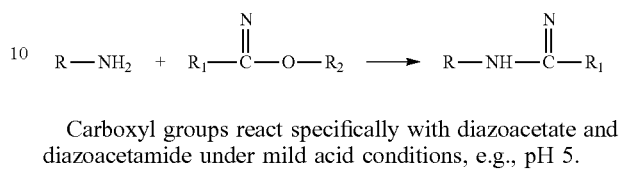

Carboxyl groups react specifically with diazoacetate and diazoacetamide under mild acid conditions, e.g., pH 5.

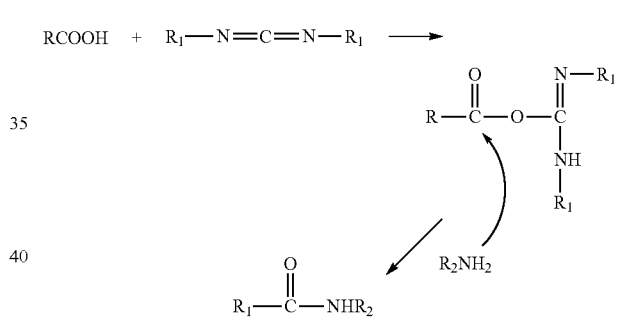

The most important chemical modification of carboxyls uses carbodiimides, such as 1-cyclohexyl-3-(2-morpholinyl-4-ethyl)carbodiimide (CMC) and 3-(3-dimethylaminopropyl)carbodiimide (EDC). In the presence of an amine, carbodiimides form an amide bond to the carboxyl in two steps. In the first step, the carboxyl group adds to the carbodiimide to form an O-acylisourea intermediate. Subsequent reaction with an amine yields the corresponding amide.

A particularly important carbodiimide reaction is its use in activating carboxyls with N-hydroxysuccinimide to form an N-hydroxysuccinimide ester.

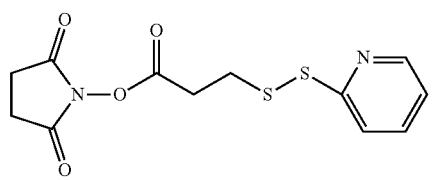

-continued

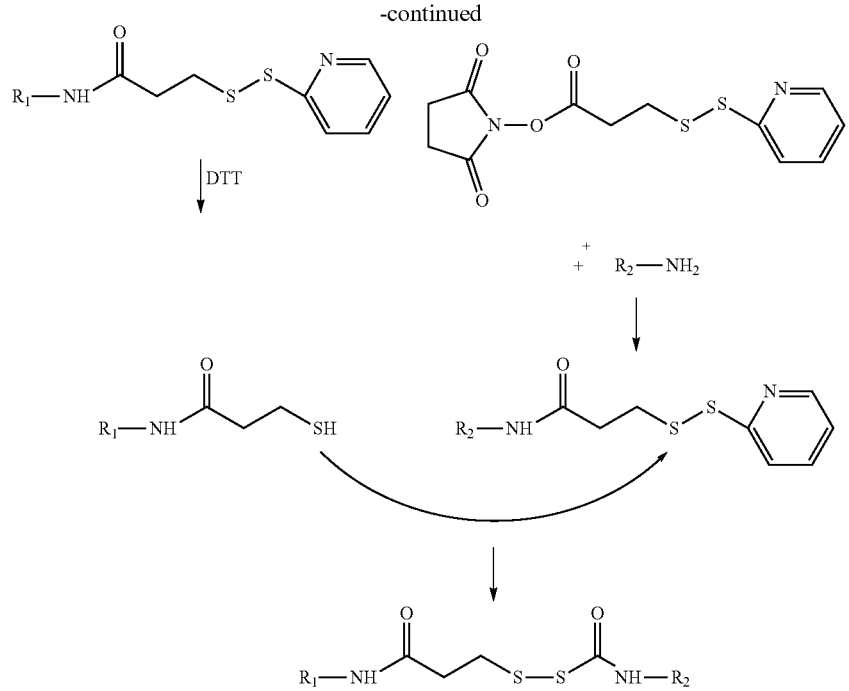

Arginine reacts with vicinal dialdehydes or diketones, such as glyoxal, 2,3-butanedione, and 1,2-cyclohexanedione. Borate may stabilize the adduct, if stabilization is desired.

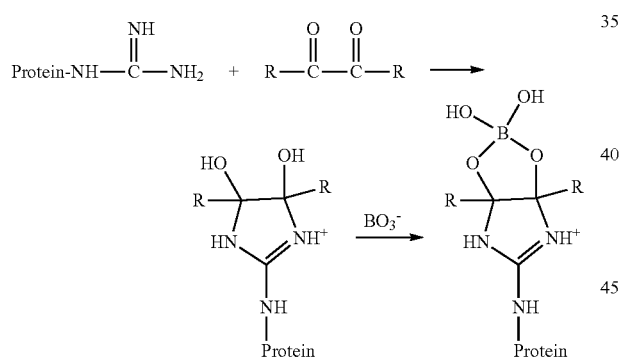

The reactive groups can also be interchanged with other reactive groups by some of the above reactions. For instance, modification of an amino group with an acid anhydride such as succinic anhydride, replaces the positively charged amino group with a free carboxyl group. Likewise, reaction of a carboxyl group with a carbodiimide and a diamine, such as ethylene diamine, replaces the carboxyl group with a free amino group.

Cross-Linking:

Reagents containing two of the reactive groups described above, for instance two amino-reactive groups or an amino-reactive and a thiol-reactive group, can be used to cross-link a chemotherapeutic agent containing one of the appropriate groups to an insulin or IGF-1 receptor ligand containing the other appropriate group. In addition, a carboxyl (of, e.g., a chemotherapeutic agent) activated with a carbodiimide or a carbodiimide and N-hydroxysuccinimide can react with an amino group (of, e.g., a protein ligand) to form an amide bond cross-link.

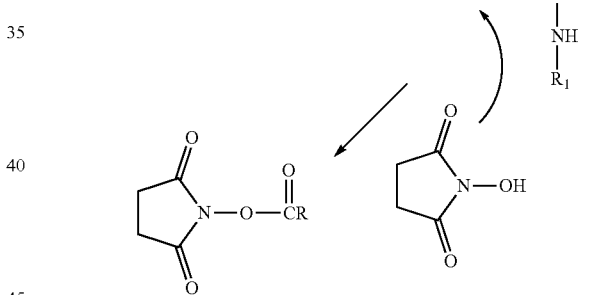

The activated carboxyl is stable enough to be isolated, but will then readily react with amino groups to form an amide bond.

Succinimides such as N-succinimidyl-3-[2-pyridyldithio] propionate (SPDP) can be used to couple two compounds through amino groups. (See Pierce Biotechnology catalog, and Thorpe, P. E. et al. 1982, *Immunol. Rev.* 62:119-158.)

EXAMPLES

Example 1

Plasmids were synthesized by DNA 2.0 (Menlo Park, Calif.) encoding these proteins with nucleotide sequences optimized for expression in *E. coli*, and under the control of a T7 promoter:

| Protein encoded | Description | Sequence |
| --- | --- | --- |
| 403IGF | His6-IGF | SEQ ID NO: 8 |
| 764IGF | His6-K5-IGF132 | SEQ ID NO: 11 |
| 765IGF | His6-K5-R3IGF | SEQ ID NO: 2 |
| 784IGF | mutTrx-R3IGF | SEQ ID NO: 9 |
| 785IGF | mutTrx-IGF132 | SEQ ID NO: 10 |

E. coli BL21(DE3) was transformed with each of the plasmids and transformants isolated. 10 ml of the transformed BL21(DE3) culture of each was used to seed 500 ml of LB media with 50 ug/ml kanamycin (LB-kan) in a 2 L baffled flask. These were induced with 0.4 mM final IPTG at an O.D. 600 nm of 0.6 and grown overnight at 25 degrees C.

The cells were resuspended in 50 mM Tris-HCl pH 8.0 and frozen. They were thawed and incubated at 5% wet weight/volume cell weight in 50 mM Tris-HCl pH 8.0, 0.2% Triton-X100, 0.5 mg lysozyme per g cell paste, for 30 minutes at room temperature. They were then sonicated to break cells. $MgCl_2$ was added to 3 mM final concentration and 250 ul of BENZONASE was added per liter of culture. This was incubated a further 1 hour at room temperature.

Inclusion bodies were isolated by centrifugation. Soluble fraction was retained.

Inclusion bodies were solubilized in 7 M urea, 0.5 M NaCl, 20 mM phosphate pH 7.8.

The solubilized inclusion bodies were loaded onto 1 ml of Ni-nitrolito-triacetic acid (Ni-NTA) resin in a column. The column was washed with Ni-A buffer and eluted with Ni-B buffer.

Ni-A 6 M urea, 0.5 M NaCl, 20 mM sodium phosphate, 20 mM imidazole, pH 7.3.

Ni-B 6 M urea, 0.5 M NaCl, 20 mM sodium phosphate, 0.4 M imidazole, pH 7.3.

The protein yields were:
403IGF eluate 3.6 mg
764IGF eluate 16 mg
765IGF eluate 24 mg
784IGF eluate 6.7 mg
785IGF eluate 1.9 mg SDS-PAGE was run of the eluates and of the crude insoluble and soluble fractions. It appeared that 784IGF and 785IGF had about half of the IGF in the soluble fraction and half in the insoluble. 403IGF, 764IGF, and 765IGF appeared to have nearly all of the IGF in the insoluble fraction.

From this data, the best yield was with 765IGF. Those with the SEQ ID NO:1 leader sequence (764IGF and 765IGF) gave better yields than those with a simple Met-His6 leader (403IGF) or with thioredoxin leader sequences (784IGF and 785IGF). And the constructs with the R3IGF mutant for the IGF portion (765IGF and 784IGF) gave better yields than the corresponding constructs with the IGF132 mutant for the IGF portion of the fusion protein (764IGF and 785IGF).

Example 2

Refolding and Binding Assay 2 ml of each of the original Ni eluates from Example 1 was mixed with about an equal volume of 100 mM glycine, 6 M urea, pH 9.5, concentrated by ultrafiltration in a CENTRICON 3 kDa filter unit, then brought up again in that buffer and concentrated to about 420 ul. Then they were diluted to 2 mg/ml for 403IGF, 764IGF, and 765IGF, and 4 mg/ml for 784IGF and 2.4 mg/ml for 785IGF.

200 ul of each of these was mixed rapidly with 1.8 ml of refold buffer. Refold buffer was 1.4 M urea, 100 mM glycine, 0.5 M NaCl, 19% ethanol, 0.5 mM GSSG, 4 mM GSH, pH 9.5. They were refolded at room temperature for 3 hours, and then tested in a binding assay for competition binding to IGF receptors against I-132 radioactive wild type IGF (Perkin Elmer, Inc.) For comparison, commercial Long-R3-IGF (LR3IGF) was also tested.

The approximate binding constants ($K_D$s) in this experiment were these:

| | |
| --- | --- |
| LR3IGF | 1 nM |
| 403IGF | 2 nM |
| 764IGF | 100 nM |
| 765IGF | 10 nM |
| 784IGF | 3 nM |
| 785IGF | 40 nM |

The fusion proteins containing the R3IGF mutant (LR3IGF, 765IGF, and 784IGF) had lower $K_D$s than those containing the IGF132 mutant (403IGF, 764IGF and 785IGF).

Example 3

Purification and Yield of 765IGF

A plasmid encoding 765IGF with optimized codon usage for E. coli, with the 765IGF gene under the control of a T7 promoter, was synthesized by DNA 2.0 (Menlo Park, Calif., USA). E. coli Bl21(DE3) was transformed with the plasmid and grown in fermentor culture and induced with IPTG.

765IGF was purified under denaturing conditions by ion exchange chromatography and Nickel affinity chromatography. The yield of purified 765IGF was about 60 mg per liter of culture.

765IGF was refolded by a procedure similar to that of Example 2 and then the refolded protein was purified by ion exchange chromatography on a DEAE resin and affinity chromatography on a nickel resin.

Example 4

765IGF Binding Assay to IGF-1 Receptor

Method:

Theory of assay: Radioactive $^{125}I$ labeled insulin-like growth factor-1 (IGF-1) competes with a test ligand for binding to type 1 IGF receptors that are abundant on MCF7 cells (a human breast cancer cell line) in vitro. The tested ligands include our 765IGF variant of insulin-like growth factor-1 (IGF-1) and our novel covalent conjugates that contain the antifolate drug methotrexate coupled to 765IGF, as well as commercially available long-R3-IGF-1 (Sigma Aldrich, St. Louis, Mo., USA) as a comparison and positive control.

MCF7 cell media: 500 mL MEM, 0.01 mg/mL bovine insulin; 5 mL sodium pyruvate, 5 mL non-essential amino acids, 10 mL sodium bicarbonate, 10 mL fetal bovine serum, 5 mL penicillin/streptomycin.

MCF7 cells (ATCC HTB-22) were plated at 20,000 cells per well in a volume of 0.5 mL/well in a 48-well tissue culture plate (flat bottom with low evaporation lid) and placed in a cell culture incubator set at 37° C. with 5% $CO_2$. After 2-3 days in culture the plates were washed 2× with 0.5 mL per well of cold binding assay buffer (100 mM Hepes-NaOH, pH 7.2; 120 mM NaCl; 5 mM KCl; 1.2 mM MgSO4;

0.1% BSA). After the final wash, 0.5 mL of binding assay buffer was added to each well and the plates are placed at 4° C. for 2 to 6 hours.

Test ligands were prepared at a concentration of 10 micromolar (long-R3-IGF) or 20 micromolar (765IGF and IGF-MTX) in 5 mM HCl in a volume of 200 ul. To determine the concentration, the molecular weight of 765IGF (9742 daltons) and long-R3-IGF (9111 daltons) are used. For long-R3, the lyophilized commercial material is dissolved at 1.0 mg/ml in 10 mM HCl and this is diluted to a concentration of 91 ug/ml for a 10 uM solution.

The 765IGF and long-R3-IGF were diluted into binding buffer in the wells at concentrations of 2000 nM to 1 nM.

Next, 25 uCi lot of I-125 IGF (Perkin Elmer Radiochemicals, Waltham, Mass., USA) was dissolved in 1 ml of water. An appropriate dilution into binding buffer was made, and then 50 ul of diluted radioactive IGF is added to each well, to add 0.03 uCi or more per well. For fresh I-125 IGF, per plate used 100 ul of the 1 ml solution of I-125 IGF in water can be added to 2.6 ml of binding buffer per plate used, and 50 ul added per well.

The plates were then incubated overnight at 4° C. Then the liquid was withdrawn from each well with a micropipettor and the wells were washed twice in binding buffer. Cells were lysed with 0.5 mL 300 mM NaOH, 1% SDS and the lysates were counted on a gamma counter.

Figure 2:
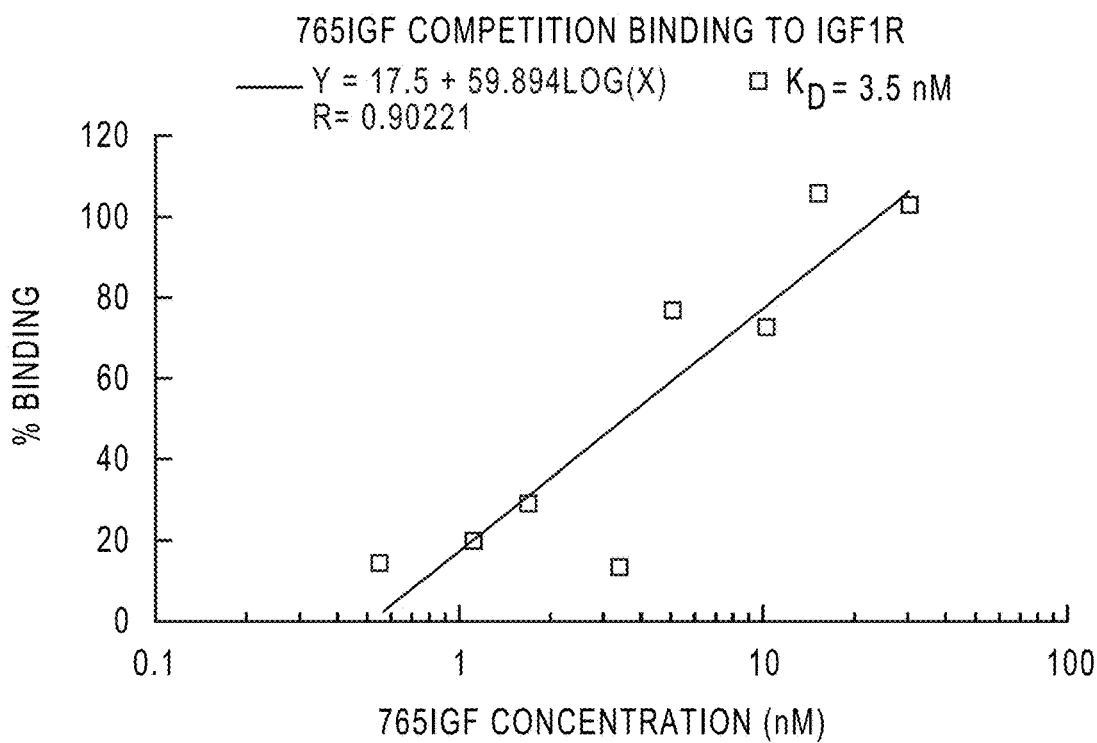
FIG. 2. Competition binding assay of 765IGF to IGF1R on MCF7 cells versus I-125-labeled IGF1.

Results:

The result of an IGF-1 receptor binding assay for 765IGF and commercially available long-R3-IGF are shown in FIG. 1. At high concentrations, 765IGF consistently displaced more radioactivity than long-R3-IGF, suggesting it may bind to IGF-1 binding sites on the membranes that long-R3-IGF does not. The $K_D$ of 765IGF in this assay was less than 1 nM, while the $K_D$ of long-R3-IGF was about 3 nM. A second binding assay with a different lot of 765IGF is shown in FIG. 2 and gave a $K_D$ of 3.5 nM.

Example 5

Conjugation of Methotrexate to 765IGF

The protein was buffer exchanged into pH 7.3 conjugation buffer and adjusted to a concentration of 2.5 mg/ml.

pH 7.3 conjugation buffer: 25 mM sodium phosphate, 10 mM NaCl, 6 M urea, pH 7.3.

pH 6.3 conjugation buffer is the same buffer at pH 6.3.

Methotrexate was dissolved at 20 mg/ml in pH 6.3 conjugation buffer, and the pH adjusted to pH 6.3 with NaOH.

1-ethyl-3-[3-dimethylaminopropyl]carbodiimide hydrochloride (EDC) was freshly dissolved in pH 6.3 conjugation buffer at 75 mg/ml.

One volume of EDC solution was added to 1 volume of MTX solution and incubated 30 seconds at room temperature and then this mixture was added to 8 volumes of 2.5 mg/ml protein solution in pH 7.3 conjugation buffer.

The mixture was mixed and then reacted overnight at room temperature. Then 6 M HCl was added to the reaction mixture to 60 mM final concentration. Then the reaction mixture was buffer exchanged into 10 mM HCl.

Result:

The amount of methotrexate conjugated per mole of protein was determined by measuring absorbance of the conjugate at 305 nm in 100 mM HCl, using a molar extinction coefficient for methotrexate groups of 21.6 per mM (Chamberlin et al. Analytical Profiles of Drug Substances, 1976, 5:283-306.) The protein concentration was determined by quantitative amino acid analysis. By this, the molar ratio of MTX groups to IGF in the 765IGF-MTX conjugate was approximately 8.

Example 6

765IGF-MTX In Vitro Cytotoxicity Assay

Cytotoxicity Assay.

This potency assay is an assay for inhibition of proliferation of MCF-7 tumor cells in vitro by incubation with the 765IGF-MTX.

Method

Day 0.

Five-thousand MCF7 cells were plated per well in a 96-well test plate in 100 ul of rich media on day 0.

Day 1.

A shadow plate was made for each test plate, with each well of the shadow plate containing media or 3× the intended final concentration of test agent in media in each well. As a negative control, media is used. As a positive control, free methotrexate at 3 uM is used.

After making the shadow plate, 50 ul is transferred from each well of the shadow plate to the corresponding well of the test plate to generate the final concentrations of test agent in the wells of the test plate.

Day 5.

Cell proliferation is determined by adding Dojindo CCK-8 reagent and incubating and measuring absorbance of the dye according to the manufacturer's instructions.

Figure 3:
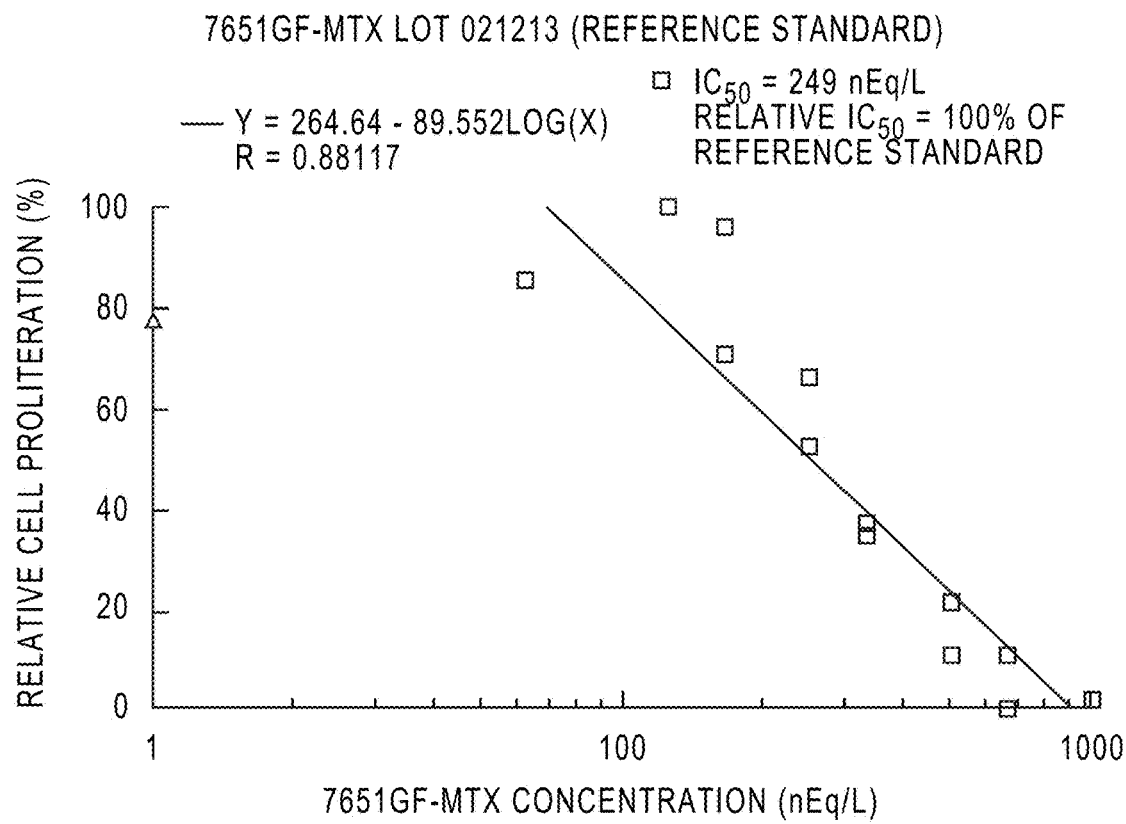
FIG. 3 shows a plot of MCF7 cell growth inhibition by 765IGF-MTX used to determine an $IC_{50}$ of 765IGF-MTX for growth inhibition.

Result:

Results of a representative cytotoxicity assay with 765IGF-MTX are shown in FIG. 3. The $IC_{50}$ (Concentration needed for 50% inhibition of cell proliferation) of 765IGF-MTX was 249 nEquivalents per L. (A nanoEquivalent is a nanomole of methotrexate groups conjugated to 765IGF.) For comparison, in the same assay, the $IC_{50}$ of free methotrexate was measured as 88 nM.

Example 7

Inhibition of Dihydrofolate Reductase by Methotrexate and IGF-Methotrexate Conjugates Method:

The experiments were done with the dihydrofolate reductase assay kit from Sigma-Aldrich (St. Louis, Mo., USA), according to the manufacturer's instructions. In the assay dihydrofolate reductase is mixed with pH 7.5 buffer. Next the inhibitor—methotrexate or an IGF-methotrexate conjugate—is added and the solution mixed. It was incubated for 30 seconds to allow inhibitor binding. Then NADPH is added to 50 uM final concentration, and then dihydrofolic acid is added to 60 uM final concentration. The reaction is monitored by measuring absorbance at 340 nm.

Results:

The tested conjugates were:

765IGF-MTX prepared as described in Example 3. 765IGF has 9 amino groups available to conjugate to methotrexate (8 lysines and the N-terminal amino group). This batch had a MTX:protein molar ratio of 7.5.

765IGF-MTX ⅓. This conjugate was prepared with ⅓ of the usual concentrations of MTX and EDC in the conjugation reaction. It produced a conjugate with a MTX:protein molar ratio of 1.2.

LR3IGF-MTX. In this case, the version of IGF is long-R3-IGF. This has 4 available amino groups for conjugation (3 lysine side chains and the N-terminal amino group). This conjugate had a MTX:protein ratio of 2.8.

In addition, free methotrexate was tested.

The conjugates were exhaustively ultrafiltered to remove any free methotrexate before their use in the inhibition assay.

Figure 4:
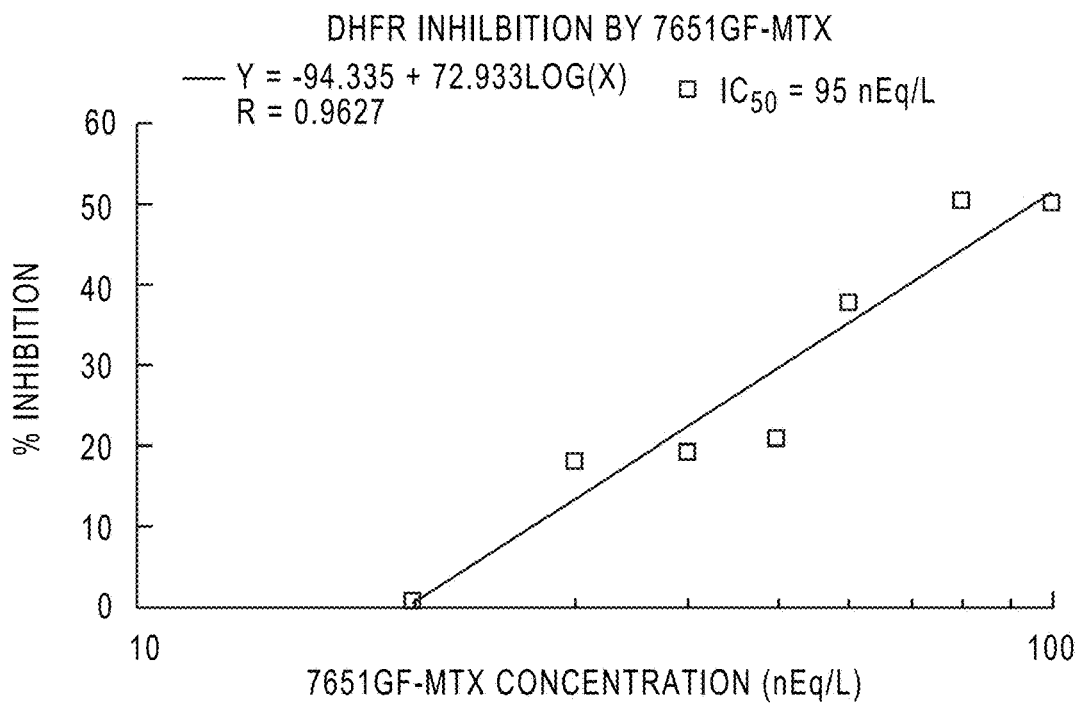
FIG. 4 shows the results of an assay for inhibition of dihydrofolate reductase (DHFR) by 765IGF-MTX.

A plot of the inhibition data for 765IGF-MTX is shown in FIG. 4.

The $IC_{50}$s of methotrexate and the conjugates were these:

| Competitor | $IC_{50}$ | MTX:IGF ratio |
|---|---|---|
| Methotrexate | 5.3 nM | N.A. |
| 765IGF-MTX | 95 nEq/L | 7.5 |
| 1/3 765IGF-MTX | 90 | 1.2 |
| LR3IGF-MTX | 99 | 2.8 |

The $IC_{50}$ in nEq/L was approximately the same for all three of the IGF-MTX conjugates, despite having different numbers of MTX groups conjugated per IGF protein monomer. This shows that each conjugated methotrexate group acts as an independent inhibitor of the enzyme. If the additional methotrexate groups on a conjugate monomer were sterically unable to bind to and inhibit a DHFR enzyme once one group is bound to a DHFR enzyme, then one would expect that the $IC_{50}$ for the conjugates would be the same in terms of nM protein concentration for each of the conjugates, instead of being the same in terms of nEq/L MTX group concentration, as is observed. Because the inhibition is proportional to MTX groups, 765IGF-MTX, with its higher MTX loading, has an inhibition constant in terms of protein concentration of 13 nM (95 nEq/L divided by 7.5 MTX per IGF gives 13 nM IGF), whereas LR3IGF-MTX has an inhibition constant in terms of protein concentration of 35 nM. Thus, with the higher loading of MTX, less 765IGF protein needs to be used to achieve the same inhibition of DHFR, and by inference the same level of killing of tumor cells.

The data show that the protein-conjugated MTX groups inhibit DHFR, but a higher concentration is needed for inhibition as compared to free MTX.

Example 8

Binding of 765IGF-MTX to IGF-1R on MCF7 Cells

Figure 5:
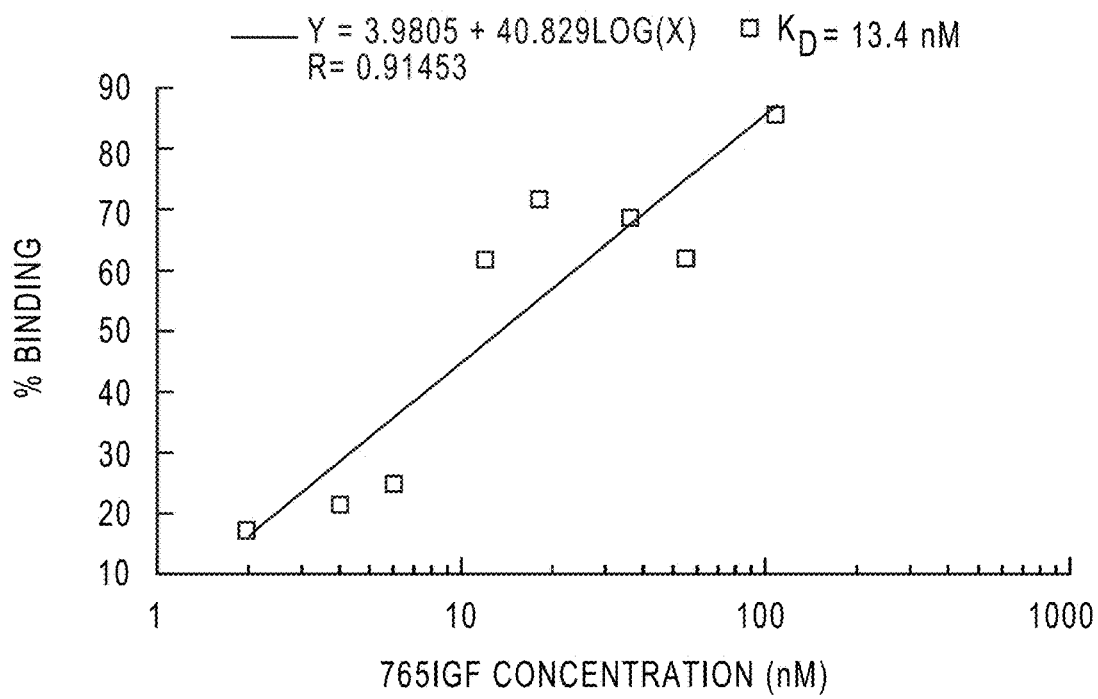
FIG. 5. Competition binding assay of 765IGF-MTX to IGF1R on MCF7 cells versus I-125-labeled IGF1.

Several competition binding assays of 765IGF-MTX conjugate with MCF7 against radiolabeled IGF-1 have been conducted, as described in Example 4. The results are a $K_D$ of about 20 nM 765IGF-MTX. (To explain, this is nM of the protein conjugate, not nEq/L of MTX groups. Since there are about 8 MTX per 765IGF, 20 nM 765IGF-MTX is about 160 nEq/L 765IGF-MTX). In the particular binding assay shown in FIG. 5, the $K_D$ was 13.4 nM.

Example 9

In Vivo Toxicology Studies

MTD is based on both non-rodent and rodent studies. Formal GLP toxicity in vivo studies were completed in rats and Beagle dogs, in which the 765IGF-MTX conjugate was administered intravenously by a single 30 minutes infusion on study Days 1 and 8 as shown in Table 1 for the dogs:

TABLE 1

| | Preparation[1] | | | |
|---|---|---|---|---|
| Group/Dose | Target Concentration µeq/ml (µmol MTX groups/mL) | Amount of 4 µeq/ml (4 mM MTX groups) 765IGF-MTX Stock Solution (mL) | D5W-Added (mL) | Total Volume (mL) |
| 1. 765IGF-MTX 0.2 µeq/kg (0.2 ul MTX groups/kg) | 0.04 | 1.25 | 123.75 | 125 |
| 2. 765IGF-MTX 2.0 µeq/kg (2.0 µmol MTX groups/kg) | 0.4 | 10 | 90 | 100 |
| 3. 765IGF-MTX 0.5 µeq/kg (0.5 µmol MTX groups/kg) | 0.1 | 3.125 | 121.875 | 125 |
| 4. 765IGF-MTX 6.0 µeq/kg (6.0 µmol MTX groups/kg) | 1.2 | 37.5 | 87.5 | 125 |

Analysis of all generated data, including clinical observations, serial blood glucose determinations, and clinical pathology revealed no drug/treatment-related significant toxicity in dogs treated by intravenous infusion with 765IGF-MTX conjugate in 5% dextrose at 0.2 and 0.5 µeq/kg. In the 0.2 µeq/kg group there was only transient dyspnea and passivity noted, while in the animals treated at 0.5 µeq/kg a single episode of vomiting and diarrhea were noted, and there was also mild reddening and swelling of the skin on the head of the female dog. Treatment of dogs in these two groups was well tolerated, and any reaction to the treatment was transient and resolved by itself.

In animals dosed at 2 µeq/kg the reactions to the treatment included mild to moderate anaphylactoid and hives-type reactions, transient anorexia and weight loss, and hypoglycemia. Reactions to the treatment in the dogs dosed at 6 µeq/kg were similar to the reactions at 2 µmol/kg, but they were more severe and lasted longer. Thus, a MTD of 765IGF-MTX conjugate in Beagle dogs in this study may be considered to be 6 µeq/kg, by a single infusion over 30 minutes.

Recovery from anaphylactoid reactions and hypoglycemia in the female dog dosed at 2 µEq/kg and in both animals dosed at 6 µEq/kg, was assisted by treatments with diphenhydramine and dextrose.

Hypoglycemia in the higher dose groups was an exaggerated pharmacological effect of IGF, which was mitigated by the use of 5% dextrose as a vehicle for delivery of 765IGF-MTX conjugate. The pathogenesis of the anaphylactoid reactions was not clear, but may have been caused by either methotrexate, IGF or the combination thereof. Vomiting, diarrhea, anorexia and weight loss are known reactions to methotrexate.

The highest non-severely toxic dose in beagles was 0.5 µeq/kg. Using the conversion from doses in dogs in uEq/kg to equivalent human dose in µEq/kg, the equivalent human dose to 0.5 µEq/kg in dogs is 0.27 µEq/kg in humans.

IGF-MTX does not Cause Significant Cytopenia

Cytopenia is a particular concern for MDS, CMML, and O-AML since it is a principal sequela of these diseases. In both rat and dog repeat dose GLP toxicology testing IGF-MTX caused almost no cytopenia, even at the highest doses tested. In both rat and dog toxicology studies IGF-MTX caused a slight dose-dependent reduction in erythrocyte mass, but even at the highest doses tested erythrocyte mass was within normal ranges. In rats but not dogs neutrophils were also slightly decreased by IGF-MTX but remained within normal ranges even at the highest doses. No other hematological parameters were affected by IGF-MTX.

In the completed Phase I dose-escalation study in human solid tumor patients, a dose of 0.8 µEq/kg was found to be tolerated without any serious adverse events. Since MDS patients have greater cytopenia than solid tumor patients, and for safety of MDS patients, we are conducting a new dose escalation in this study beginning at a dose level of 0.2 µEq/kg administered on days 1, 8, and 15. See the schema on page 6 for the dose escalation schema.

Example 10

A 6-Dose, Once Weekly, Intravenous Toxicity Study with IGF-Methotrexate Conjugate in Sprague-Dawley Rats, Followed by a 14-Day Recovery Period This repeated dose study examined the systemic toxic potential and target organs for toxicity of 765IGF-MTX, a conjugate of a variant of insulin-like growth factor designated 765IGF with methotrexate (MTX). The IGF-MTX conjugate was administered once a week, for 6 weeks, by intravenous slow bolus injection. Three groups of Sprague-Dawley rats were dosed intravenously at dose levels of 0.5, 2 and 5 µEq/kg (µEq is a µmol of methotrexate groups) for two doses. Since no toxicity was observed at the high-dose group, starting from third dose, the dose level in the mid-dose group was increased from 2 to 5 µEq/kg and this remained until the end of treatment (i.e. the animals received a total of 4 doses at 5 µEq/kg). In the high-dose group, the dose was first increased from 5 to 10 µEq/kg (third dose) and then due to severe toxicity, the dose level was adjusted to 8 µEq/kg for the remaining 3 doses. The control group of rats was dosed with 5% Dextrose Injection USP (D5W) which was used as the diluent for the IGF-MTX preparations.

Four groups of rats were used in this study (1 control and 3 test). Each Main Study test and control group consisted of 10 male rats [Strain: Crl:CD® (SD) BR-Sprague-Dawley (Charles River Canada Inc., Canada)]. There were also 5 rats per sex included in the Recovery groups in the control, mid and high-dose groups; and 3 rats per sex (control) and 6 rats per sex per group (test groups) in CBC/glucose subgroups. An additional 3 rats per sex were allocated to the control group and 9 rats per sex to each test group for toxicokinetics blood collection.

The dose volume was 4 mL/kg, for all groups including the control group. Although some adjustments to the dose levels were made for the purpose of this report, the doses used in the report will be referred as 0.5, 5 and 8 µEq/kg.

Examinations of all animals included daily clinical observations, and daily food and water monitoring. Animals also received detailed physical examinations on a weekly basis. Body weights were recorded initially and then on Days 7, 14, 21, 28, 35 and 41, and prior to necropsy on Day 42 (Main Study animals), and additionally on Days 37, 42, and 49 and prior to necropsy on Day 50 (Recovery animals). Food consumption was recorded weekly. Complete blood count (CBC) was performed 24 hours before the second dose, and 24 hours prior to each subsequent dose. Complete clinical pathology was performed at the end of the Main Study and Recovery Periods.

Ophthalmoscopy was performed initially (before the initiation of treatment), and at the end of the Main Study.

Blood samples were also collected as per the protocol schedule for toxicokinetics, however the samples were not analyzed. Six days after the end of the sixth dose, 10 male and 10 female Main Study animals from each group were euthanized and submitted for gross necropsy and histopathology examinations. The remaining 5 male and 5 female Recovery rats in the control group, and the groups dosed at 5 and 8 µEq/kg were euthanized 14 days after the last dose and were submitted for necropsy and histopathological examinations.

Three rats died and/or were euthanized in the high-dose group. On Day 15 (Dose 3) when the dose was increased from 5 to 10 µEq/kg one male (TK group) and one female (Main Study group) died immediately after the dosing was completed.

It was suspected that the low pH of the test article (pH~2.3) may have caused metabolic acidosis after the dose level was increased to 10 µEq/kg and/or that the test article precipitated intravenously. Histopathological evaluation found numerous variably sized round greenish-gray amorphous particles, some with central densities in lungs of both animals which died acutely. One of these rats had these particles also in the heart. In both animals there was also acute thromboembolism in lungs, and acute intravenous coagulation in the heart. It appears that the injected material precipitated and initiated intravascular platelet aggregation with micro embolism and obstruction of small blood vessels.

In the third rat that was euthanized on Day 24, ascending pyelonephritis with ischemic necrosis and parenchimal atrophy were found. These changes were severe and explained the clinical deterioration. This condition was considered incidental and not related to the treatment with the test article.

With the exception of the rats that died, all other rats from all groups received the specified treatment and survived to the scheduled euthanasia and necropsy dates.

There were no treatment-related systemic toxic effects in any rat treated with IGX-MTX conjugate at 0.5 µEq/kg, or in rats dosed at 2 µEq/kg (for the first 2 doses), and then at 5 µEq/kg for the remaining 4 doses.

In the high dose group occasional haematuria was observed in some rats after the dose was increased to 10 µEq/kg within one hour after dosing. This was attributed to the low pH (pH=~2.3) of the test formulation.

Ophthalmology results did not identify any abnormal findings, and food consumption and body weight gains did not identify any significant differences between the test and control groups.

Pathology findings that were most likely treatment-related in the groups dosed at 5 and 8 µEq/kg, but were expected and common adverse reactions to MTX administration, were as follows:

The general trend in CBC parameters monitored during the study was a slight dose-dependent decrease in erythrocyte mass (RBC's, Hb, Hct), with a compensatory increase in reticulocytes. Before Dose 6, erythrocyte mass in the group treated at 5 µEq/kg was reduced by approximately 8-15%, (gender combined), and there was approximately 15-19% decrease in the group dosed at 8 µEq/kg. At the same time, reticulocyte counts increased 47-102% and 2.2-2.4-fold, (gender combined), in the groups which received the IGF-MTX conjugate at 5 and 8 µEq/kg, respectively. Neutrophil counts were also decreased in both these groups.

Reduction in erythrocyte mass was also observed at the end of the Main Study in animals of both genders in the groups treated with IGF-MTX conjugate at 5 and 8 µEq/kg (mean decreases of 6-7%, and 10-14%, for the groups that were dosed at 5 and 8 µEq/kg, respectively). Compensatory reticulocytosis was noted in both of these groups.

WBC's were also decreased in these 2 groups (neutrophils, lymphocytes and monocytes were all affected). All cell types appeared about equally affected. The reduction in neutrophils was about 5-35% (gender combined) in the group treated at 5 µEq/kg, and in the group that was dosed at 8 µEq/kg, the decrease ranged between 50-57%, when compared to the controls. Platelets were also significantly decreased in females dosed at 8 µEq/kg (approximately 38% decrease relative to the control females). In the recovery animals, all these parameters were either back to normal or were showing the tendency of normalization indicating recovery.

The mean weight of the spleen was increased in both males and females dosed at 5 and 8 µEq/kg. The increases ranged on average between 17 to 38%, relative to the mean weight of the spleen in the control rats.

The changes that were observed in treatment groups, and which were considered treatment-related, but were expected exaggerated pharmacological effects of IGF, were as follows:

In the group dosed at 0.5 µEq/kg (gender combined) mean glucose levels were increased after dosing. The increases ranged between 0.3±0.5 to 4.0±5.0 mmol/L, over 6 doses. Occasionally, in some individual animals there was a decrease in blood glucose levels in this group.

In the group dosed at 5 µEq/kg, the mean increases or decreases in blood glucose levels over 6 doses, ranged between −1.8±7 to 7.5±3.4 mmol/L, and in the group dosed at 8 µEq/kg, the increases/decreases ranged between −2.1±1.3 to 2.6±3.1 mmol/L. On one occasion ($3^{rd}$ dose—10 µEq/kg) glucose levels in some animals decreased below 2.8 mmol/L, and thus all animals in this group were dosed with 10% Dextrose, I.P. at 2 mL/rat. It should be noted that decreases in glucose blood levels appeared dose dependent.

Histopathological evaluations identified some changes in the lungs of animals dosed at 8 µEq/kg that may be of possible toxicological significance and these were as follows:

In the lungs, there was increased prominence of small blood vessels with infiltrates of granulocytes and lymphocytes in the perivascular interstitium in many animals in the study. These perivascular inflammatory cell infiltrates were observed in 5/20 controls and in 19/19 in the group dosed at 8 µEq/kg animals in the Main Study. The severity of this response was higher in the group dosed at 8 µEq/kg. The response was seen in 4/10 controls and 0/10 high-dose animals in the Recovery groups.

In one animal in the high-dose Recovery Group, there were wedge-shaped areas of parenchymal loss with replacement fibrosis consistent with ischemic infarcts. These are the residuum of an earlier focal ischemic event. It is unknown whether the infarcts were related to the treatment, because such changes could occur as a sporadic condition unrelated to the protocol.

In conclusion, analysis of all generated data, including clinical observations ophthalmology, gross necropsy and histopathology revealed no drug/treatment-related significant toxicity in rats that were treated intravenously with IGF-MTX conjugate at 0.5 and 5 µEg/kg weekly, for 6 weeks. At these two dose levels, the treatments were well tolerated by animals.

At a dose level of 0.5 µEg/kg, the only finding that was occasionally noted in some rats was a marginal decrease in blood glucose levels. This finding was an expected pharmacological effect of IGF, and thus under the conditions of this experiment, the no observed effect level in this study was considered to (NOEL) be equal to 0.5 µEq/kg dosed weekly, for 6 weeks.

At a dose level of 5 µEq/kg, besides the decrease in blood glucose levels which were more pronounced than in the animals dosed at 0.5 µEg/kg, there was also a marginal decrease in erythrocyte mass (about 8-15% before Dose 6, and about 6-7% at the end of the Main Study). WBC's were also marginally reduced in this group at the end of the Main Study (about 5-35%). At the end of recovery both RBC's and WBC's were within the normal ranges in this group, indicating the reversibility of these changes. There was also a marginal increase in the weight of spleens in this group, which showed a tendency for normalization in the Recovery animals. These findings were known effects of MTX on hematopoiesis. Thus, under the condition of this experiment, the no observe adverse effect level (NOAEL) in this study was considered to be equal to 5 µEg/kg.

Example 11

A 5-Dose, Once Weekly, Intravenous Infusion Toxicity Study with IGF-Methotrexate Conjugate in Beagle Dogs, Followed by a 21-Day Recovery Period This repeated dose study examined the systemic toxic potential and target organs for toxicity of 765IGF-MTX, a conjugate of a variant of insulin-like growth factor designated 765IGF with methotrexate (MTX). The IGF-MTX conjugate was administered once a week, for 5 weeks, by intravenous (IV) infusion. Three groups of Beagle dogs were dosed intravenously at dose levels of 0.5, 2 and 4 µEq-kg (a µEq is a µmole of methotrexate groups) in 5% dextrose (D5W), and the fourth control group of dogs was dosed with D5W which was used as the diluent for the IGF-MTX conjugate preparations.

Four groups of dogs were used in the study (1 control and 3 test groups). The control group, mid-dose and high-dose groups consisted of 10 dogs (5 males and 5 females), and the low-dose group consisted of 6 dogs (3 males and 3 females), breed: Beagle, Ridglan Farms. The test and control articles were administered by an IV infusion at a dose volume of 5 mL/kg/hour over 1 hour.

Examinations of all animals included daily clinical observations, and daily food and water monitoring. Animals also received detailed physical examinations on a weekly basis. Body weights were recorded initially and then on Days 8, 15, 22, 29 and 34 and prior to necropsy on Day 35 (Main Study animals), and additionally on Days 30, 37, 44, 49 and prior to necropsy on Day 50 (Recovery animals). Food consumption was recorded daily. Complete blood count (CBC) was performed 24 hours after the first dose, and prior to each subsequent dose. Complete clinical pathology was performed before study initiation, at the end of the Main Study and Recovery Periods.

All animals received the specified treatments at doses of 0.5 to 4 µEq/kg and no mortalities were associated with the treatments.

Ophthalmology and ECG's (including QT) findings were found to be within the normal physiological limits in all test groups.

In the group dosed at 0.5 µEq/kg, clinical reactions to the treatment were mild and consisted of mild to moderate passivity and injected sclera in one male dog, vomiting in two female dogs, and mild dyspnoea in another female dog. Mild edema around the eyes was also observed in one female animal. All of the above observations were single clinical events, which occurred only once during the 5 dose periods, were transient and resolved themselves. Any decrease in blood glucose levels after dosing in these animals was negligible. At the end of study, there was a minimal reduction in erythrocyte mass noted in this group (about 10% reduction, compared to the controls). However, Red Blood Cells (RBC's), Hematocrit (Hct) and Hemoglobin (Hb) in this group were well within the normal ranges. These findings were not considered clinically relevant as they were of low magnitude, transient, resolved themselves and were the expected side effects of methotrexate therapy.

Clinical findings, clinical pathology, and gross necropsy which were treatment-related in the groups dosed at 2 and 4 µEq/kg that were clinically relevant, but were expected and common adverse reactions to MTX administration, were as follows:

Post-dosing anorexia was observed in all dogs, with subsequent reduction in body weights, and/or body weight loss. In dogs dosed at 2 µEq/kg, anorexia was observed usually on the second day after each dosing, which would last for a couple of days, and then the animals would completely or partially recover by the next dose. By the end of the Main Study, the body weight gain in these dogs was negligible, male animals gained only about 1.2% compared to 8.4% for the control male dogs, over the 34-day period, and females gained 2.8% in comparison to 11.1% for the control females. Food consumption in this group was approximately 22% lower (gender combined) than the food consumption of the control dogs.

In animals dosed at 4 µEq/kg, anorexia was more severe than in the dogs dosed at 2 µEq/kg. This resulted in approximately 36-38% reduction in food consumption over the treatment period, when compared to the controls, and the total average weight loss in dogs was 1.3 kg for males and 0.9 kg for females. During the 3-week Recovery Period, dogs from this group regained their body weights, indicating reversibility.

Occasionally nausea (retching), diarrhoea and vomiting were observed in some animals dosed at 2 µEq/kg and in all dogs dosed at 4 µEq/kg. These were usually observed on days when dosing was performed.

Reduction in erythrocyte mass (RBC's, Hb, Hct) and anisocytosis/macrocytosis was mild by the end of the Main Study. The reduction was approximately 13% and 15%, for dogs dosed at 2 and 4 µEq/kg, respectively, when compared to the control dogs. By the end of the Recovery Period, the erythrocyte mass was still below the pre-study levels in these two groups. However, the reduction in RBC's, Hb and Hct levels never exceeded the lower limits of the normal ranges.

The mean total protein and albumin levels were reduced slightly below the limit of normal ranges in animals dosed at 4 µEq/kg. After the Recovery Period, these levels were within the normal ranges. Reduced albumin levels were most likely the result of anorexia and body mass loss as reported in these dogs.

In 2 out of 10 dogs dosed at 2 µEq/kg, ALT activity was slightly increased above the upper limit of normal ranges (on average 11% increase). In dogs dosed at 4 µEq/kg, 4 dogs were affected and increases were approximately 1-fold for males and about 52% for females, on average. In the absence of histopathological findings indicating hepatocellular injury, the increases of ALT most likely represented sublethal injury with alterations in hepatocyte permeability, and an increase in ALT.

Glucose level decreases in the group dosed at 2 µEq/kg (initial blood glucose level minus blood glucose level immediately after the end of infusion) ranged between −2.5±1.3 to −0.7±1.3 mmol/L (mean decrease over 5 doses, gender combined). In the group dosed at 4 µEq/kg, the decreases ranged between −3.9±1.7 to −1.6±0.6 mmol/L. The decreases in blood glucose levels were an expected pharmacological effect of IGF.

Clinical and pathology findings that were considered dosing and treatment-related, and which were clinically relevant and toxicologically significant in the groups dosed at 2 and 4 µEq/kg, are described below. It should be noted that the following adverse reactions are less common, but are known and reported reactions in humans receiving MTX for various conditions. However, it cannot be completely excluded that the following reactions were not augmented by the presence of IGF. These reactions were as follows:

Anaphylactoid (angioedema), type of reactions presented as swelling (edema) and reddening (erythema) of the skin of head (around the eyes, lips, ears), throat, neck and forelimbs, were noted mostly during the infusion. The total number of dogs that had these reactions (all groups combined) during dosing were: 5 dogs (the first dose); 3 dogs (the second dose); 4 dogs (the third dose); 14 dogs (the fourth dose) and 6 dogs (the fifth dose). It should be noted that on the fourth day of dosing, there was a spike in the number of dogs with these reactions and in the severity of the reactions, however, during the following dose (dose five), the reactions were comparable to the reactions seen on dosing Days 1, 2 and 3.

There did not appear to be a difference (qualitative or quantitative) in anaphylactoid reactions between the groups which were dosed at 2 or 4 µEq/kg of IGF-MTX conjugate.

Two dogs from the group dosed at 2 µEq/kg, had neurological reactions which consisted of a seizure in one male dog during the second dose and a transient loss of consciousness and postural tone during the third dose in one female dog. Both animals received subsequent treatment without further neurological incidents.

One plausible explanation for the seizure in one dog would be that the blood-brain-barrier (BBB) was disrupted by the release of inflammatory mediators (this animal had moderate anaphylactoid reactions to the treatment and had to be treated with antihistamines before the seizure started), and/or the BBB was disrupted by the extramedullary haematopoiesis in the choroid plexus as found histologically in this dog. The latter is reported predisposing condition for seizures in dogs. The second dog with a minor neurological incident was also found with the extramedullary haematopoiesis in the choroid plexus. Secondly, the dog with the seizure had an unexpectedly high spike of MTX in the blood during infusion. The MTX level in this dog on Day 1 was at least 2-7 fold higher than in any other dog dosed at 2 µEq/kg and it was at least 2-fold higher than in the dogs which received the test article at 4 µEq/kg. Thus, the most likely explanation for the seizure in this animal was a probable disruption of the BBB and a high spike of MTX in the blood.

Histopathologically there were several findings of potential toxicological significance and they were as follows:

Thymic atrophy due to depletion of cortical and medullary lymphocytes occurred in several dogs with increasing frequency and severity with treatment dose. Thymic atrophy was pronounced, dose-related through the 0.5-4.0 µEq/kg/week dose range, and persistent through the recovery period. While this might have occurred as a direct effect of the test article on proliferating thymic lymphocytes, thymic atrophy is best explained as an indirect stress response. Thymic atrophy was reported in humans as a response to MTX chemotherapy.

The animal in the group dosed at 2 µEq/kg that had a seizure had several findings that were not seen in other animals in the study. These included increased lymphocytic infiltrates of the superficial mucosa of the cecum and rectum, unilateral focal degeneration and mineralization of the corticomedullary region of one adrenal gland, and prominent hyperplasia with mixed leukocyte infiltrates in the respiratory epithelium of the trachea and major bronchi.

Toxicokinetic (TK) parameters for free MTX were estimated from plasma concentration-time data arising from a 5-dose once weekly intravenous infusion study with insulin-like growth factor (IGF) MTX conjugate at low (0.5 µEq/kg), mid (2.0 µEq/kg) and high (4.0 µEq/kg) MTX equivalent dose levels. No consistent differences in the plasma levels of MTX were observed between animals of different genders and thus data from males and females were combined. Plasma levels of MTX increased with time both during and following a 1-hour intravenous infusion of the IGF-MTX conjugate. On Day 1 and based on the mean plasma concentrations of 6-10 dogs, the Tmax was 2 hr from start of infusion for all dose levels. Cmax values ranged from 71.6-511.9 ng/mL. Both the AUC∞ and Cmax values were dose proportional. The plasma terminal half-life and mean residence time of MTX ranged from 4.6-5.5 hrs and 6.1-7.6 hrs, respectively, with a low apparent clearance (based on liberation of free MTX from the conjugate) and large apparent volume of distribution ranging from 0.34-0.46 L/hr/kg and 2.24-2.81 L/kg, respectively. The pharmacokinetics of MTX following Day 29 of dosing were similar to those following Day 1 of dosing.

These findings suggest that free MTX is liberated in a time-dependent manner due to metabolism of the conjugate. Thus, the resulting TK for MTX are dependent on both the liberation of MTX from the conjugate and the elimination of free MTX over time.

Following intravenous administration of the IGF-MTX conjugate in the dose range of 0.5-4.0 µEq/kg to Beagle dogs, serum levels of the IGF-MTX conjugate decreased quickly. There was no gender bias and an increase in serum exposure was observed on Day 29 compared to Day 1. The apparent clearance of the IGF-MTX conjugate which was small and ranged from 0.02-0.05 L/kg/hr, decreased by 25-50% on Day 29 compared to Day 1, while the apparent volume of distribution, also small and which ranged from 0.07-0.20 L/kg, did not display any trends. The terminal half-life of the IGF-MTX conjugate which ranged from 2.5-4.6 hrs was marginally longer on Day 29 compared to Day 1, while the mean residence time which ranged from 1.4-5.3 hrs, did not display any trend. Together these findings suggest that following intravenous administration the IGF-MTX conjugate, it was eliminated with a low clearance from a small volume of distribution consistent with its large molecular size. The elimination of the IGF-MTX conjugate was marginally slower with successive doses, resulting in an increased plasma exposure. The elimination of the IGF-MTX conjugate preceded the development of maximal MTX concentrations.

In conclusion, analysis of all generated data, including clinical observations, ophthalmology, electrocardiography, gross necropsy and histopathology revealed no drug/treatment-related significant toxicity in dogs that were treated intravenously with IGF-MTX conjugate at 0.5 µEq/kg weekly, for 5 weeks.

At this dose level of 0.5 µEq/kg, the only findings that were most likely treatment-related were mild to moderate passivity and injected sclera in one animal, vomiting in two dogs and mild dyspnoea in another dog. Mild edema around the eyes was also observed in one dog. At the end of the study, there was also a mild reduction in erythrocytes (about 10% reduction, relative to the control group). These findings were not considered clinically relevant as they were of low magnitude, transient, resolved themselves and were expected side effects of methotrexate therapy.

Therefore, under condition of this experiment, the no observed adverse effect level (NOAEL) in this study was considered to be equal to 0.5 µEq/kg dosed weekly, for 5 weeks.

In the groups dosed at 2 and 4 µEq/kg, the side effects which were also associated with the MTX administration included anorexia with reduced body weight gain or body weight loss, occasional diarrhea and vomiting. There was also a mild reduction in erythrocyte mass, (about 13-15%) and reduced albumin levels, and a slight increase in ALT activity. These observations appeared to be dose-dependent and with the exception of RBC reduction, there was a full recovery of all animals by the end of the recovery period. In these two groups, thymic atrophy and an increased number of necrotic cells in the duodenum were also noted at histopathology.

There were also two types of adverse reactions noted in this study, which although undesirable, were not completely unexpected as they were reported adverse reactions to MTX administration. In the group dosed at 2 µEq/kg, in two dogs there were neurological incidents. The first dog had a seizure during the second dose. In this animal, the seizure may have been the result of a disruption in the blood-brain-barrier, induced by inflammatory mediators and/or extramedullary haematopoiesis, and a high spike of free MTX. In the second dog, there was one episode of loss of consciousness and postural tone. In the groups dosed at 2 and 4 µEq/kg there were incidences of anaphylactoid reactions.

For the neurological and anaphylactoid reactions, although most likely induced by MTX, it cannot be completely excluded that IGF did not play any role in these events. It has to be noted that both of these adverse reactions were easily controlled by the appropriate therapy (antihistamines and diazepam).

Example 12

Phase I Study of IGF-Methotrexate Conjugate in the Treatment of Advanced Tumors Expressing IGF-1R The primary objective of this study was to determine the maximum tolerated dose (MTD) of 765IGF-MTX by evaluation of toxicity during treatment of advanced, previously treated malignancies that express IGF-1R. One inclusion criterion was that a subject's tumor (tissue, bone marrow, or blood) must express IGF-1R, defined as ≥10% of tumor cells expressing IGF-1R by immunohistochemistry (IHC). Patients were enrolled with solid tumors or lymphomas.

Nineteen subjects were enrolled in this dose escalation study. 765IGF-MTX was administered as an IV infusion over 1 hour on days 1, 8 and 15 of a 28 day cycle in 250 ml of 5% dextrose or at the physician's discretion 10% dextrose. Treatment continued until disease progression, unacceptable toxicity, or patient refusal. Assessment of response was confirmed with imaging studies performed at the end of cycle 2+/−7 days, and every 2 cycles thereafter. The table below shows, for each dose level tested, the subjects that were tested, the type of malignancies they had, number of cycles they completed, whether they experienced a dose limiting toxicity (DLT), and, if applicable, their reason for study discontinuation. One patient with Hodgkin Lymphoma at dose level 3 was treated with 22 doses with apparently stable disease by CT scan, but treatment was discontinued when a lymph node biopsy showed no evidence of cancer.

| Dose Level | Dose (µEq/kg) | Subject # | Malignancy | DLT (Y/N) | # doses | Reason for discontinuation |
|---|---|---|---|---|---|---|
| 1 | 0.05 | 1 | Colon Ca | N | 6 | Progression |
| 2 | 0.10 | 2 | Met adamantinoma | N | 6 | Progression |
| 3 | 0.20 | 3 | Colorectal, met | N | 6 | Progression |
| 3 | 0.20 | 4 | Endometrial Ca | Y | 1 | not evaluable |
| 3 | 0.20 | 5 | Endometrial Ca | N | 18 | stable disease |
| 3 | 0.20 | 6 | Pancreatic Ca | N | 2 | not evaluable |
| 3 | 0.20 | 7 | Thymic Ca | N | 6 | Progression |
| 3 | 0.20 | 8 | Hodgkin Lymphoma | Y | 6 | Progression |
| 3 | 0.20 | 9 | Hodgkin Lymphoma | N | 22* | stable disease or complete response |
| 4 | 0.40 | 10 | Colon Ca | N | 5 | Progression |
| 4 | 0.40 | 11 | Thymoma | N | 6 | Progression |
| 4 | 0.40 | 12 | Colon Ca | N | 9 | stable disease |
| 5 | 0.80 | 13 | mCRC | N | 3 | not evaluable |
| 5 | 0.80 | 14 | Pancreatic Ca | N | 6 | Progression |
| 5 | 0.80 | 15 | Colon Ca | N | 3 | not evaluable |
| 5 | 0.80 | 16 | Endometrial Ca | N | 4 | not evaluable |
| 5 | 0.80 | 17 | Colon Ca | N | 6 | Progression |
| 5 | 0.80 | 18 | Breast Ca | N | 6 | Progression |
| 5 | 0.80 | 19 | Basal cell Ca with lung mets. | N | 6 | partial response. |

*At time of this report is tumor-free by lymph node biopsy.

Adverse Events

Adverse events experienced during the prior solid tumor Phase I on solid tumor patients that were graded as possibly or probably related to the study drug are shown in the Table below.

| Adverse events possibly related to study drug | |
|---|---|
| Event | Grade |
| Hypotension | 3 |
| Fever | 2 |
| Seizure | 2 |
| Sinus tachycardia | 2 |
| Dyspnea | 2 |

| Adverse events possibly related to study drug | |
|---|---|
| Event | Grade |
| Abdominal pain or cramps | 2 |
| Nausea, Vomiting | 1 |
| Hypoglycemia | 1 |
| Dizziness | 1 |

None of the adverse events were seen in all subjects or all drug administrations in a single subject. The most common adverse events were hypoglycemia, which is an expected consequence of the study drug, chills, and fever. When these occurred, they usually resolved within 2 hours after the end of the infusion. One subject had grade 2 fever beginning with the infusion and lasting overnight. One subject had grade 3 hypotension beginning during the infusion and lasting overnight. Nausea and vomiting were common, but occurred during the infusion, not with a several hour delay as is typical with chemotherapy. In all cases they resolved within 1 hour after the end of the infusion. Abdominal pain or cramping was common but appeared limited to patients with colon carcinoma, so it may have been associated with the study drug binding to and targeting their tumor tissue. The one seizure that was seen occurred during the infusion in a subject during cycle 5, day 1 (the patient's 16th dose of drug) at dose level 0.4 uEq/kg, and resolved in 2 minutes. This patient also experienced the grade 3 hypotension event at the same time and was hospitalized overnight for it.

Absence of Cytopenia.

Remarkably, there was no evidence of any cytopenia in any subject treated.

Example 13

Cytotoxicity In Vitro Against MDS and AML Cell Lines and Synergy with Azacitidine IGF-MTX is Cytotoxic In Vitro Against an MDS Cell Line.

Figure 6:
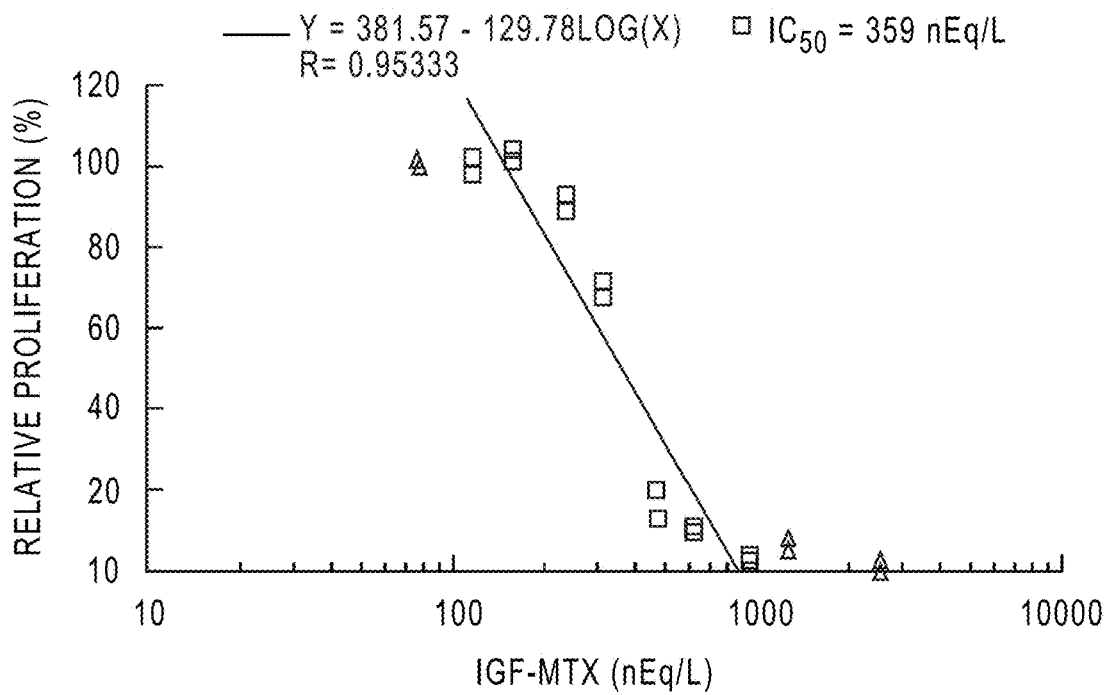
FIG. 6. is of plot of MDS-L cell growth inhibition by 765IGF-MTX.

765IGF-MTX was tested in vitro in a tritium incorporation assay. The MDS-L cell line was licensed from Dr. Kaoru Tohyama of Kawasaki Medical School, Japan. Cells were plated at 15,000 cells per well in 150 ul medium in a 96-well plate on Day 1. On day 2, IGF-MTX was added at concentrations ranging from 78 nEq/L to 15 microEq/L. On day 6, one microCi of tritiated thymidine was added per well, and after 6 hours the wells were harvested and counted. The result is shown in FIG. 6. The IC50 was 359 nEq/L. One nEq is defined as 1 nmole of MTX groups. There are approximately 8 MTX groups per 765IGF.

IGF-MTX is Cytotoxic In Vitro Against Myeloid Cancer Cell Lines and is Synergistic with Azacitidine Three AML cell lines were tested in our laboratory for sensitivity to IGF-MTX. The three cell lines were HL-60, HL-60/S4, and Kasumi-1. All three were sensitive to IGF-MTX with IC50s of 458-668 nEq/L (nM of methotrexate groups in the IGF-MTX conjugate). This is about the same as the IC50 against MCF7 breast cancer cell line and LNCaP prostate cancer cell line, both of which are sensitive to IGF-MTX in mouse xenografts.

The effect of IGF-MTX was also additive or synergistic with Azacitidine on at least the Kasumi-1 and HL-60 cell lines (it was not tested the combination on HL-60/S4). In the presence of a concentration of Azacitidine about ⅓ of its IC50, the IC50 of IGF-MTX decreased from 668 to 398 nEq/L in Kasumi-1 cell line and decreased from 466 to 409 nEq/L in HL-60.

Example 14

An MDS Cell Line has a High Level of IGF-1R

MDS-L cells were grown in RMPM1640/10% fetal calf serum/50 ng/ml IL-3, 50 micoM beta-mercaptoethanol. They were harvested when they were at a density of about 5×10^5 cells per ml are resuspended at 20 million cells per ml in 25 mM Tris, 150 mM NaCl, pH 7.5 (TBS), which was at 0.5 mg/ml protein.

MCF7 was grown in Eagle's Minimum Essential Medium, 10% FBS, 0.1 mg/ml human insulin. MCF7 were harvested in exponential phase into TBS at 1.0 mg/ml protein.

Non-reducing SDS-PAGE was run on 4-20% Tris glycine wedge gels.

The samples were diluted with 4×LDS (65 ul sample, 20 ul LDS buffer).

Lanes
1. markers 8 ul NEB P7710s prestained
2,3, blank.
4. 15 ul MCF7 sample (12 ug).
5. 3.75 ul MCF7 sample (3 ug)
6. blank.
7. 20 ul MDS sample (8 ug)

The gel was electrotransferred onto a 0.2 micron PVDF filter (Invitrogen LC2002) in 25 mM Tris, 192 mM glycine, 0.1% SDS, 20% methanol (v/v) transfer buffer.

The membrane was blocked in TBST (TBS with 0.1% Tween-20) plus 5% dry milk for hour at 23 C, then probed overnight in 0.2 microg/ml of BAF391 biotynylated mouse monoclonal antibody—against IGF-1R (RnD systems) at 4 C. The next day it was washed 3× for 12 minutes each in TBST, then incubated in 1/2,000 diluted Pierce high sensitivity streptavidin-HRP conjugate, thermo sci cat. No. 21130, diluted in 30 ml of TBST+5% milk. Tt was rocked in that for 60 minutes at room temp. Then I rinsed briefly in TBST twice and then rocked in TBST for 12 minutes 3 times.

Figure 7:
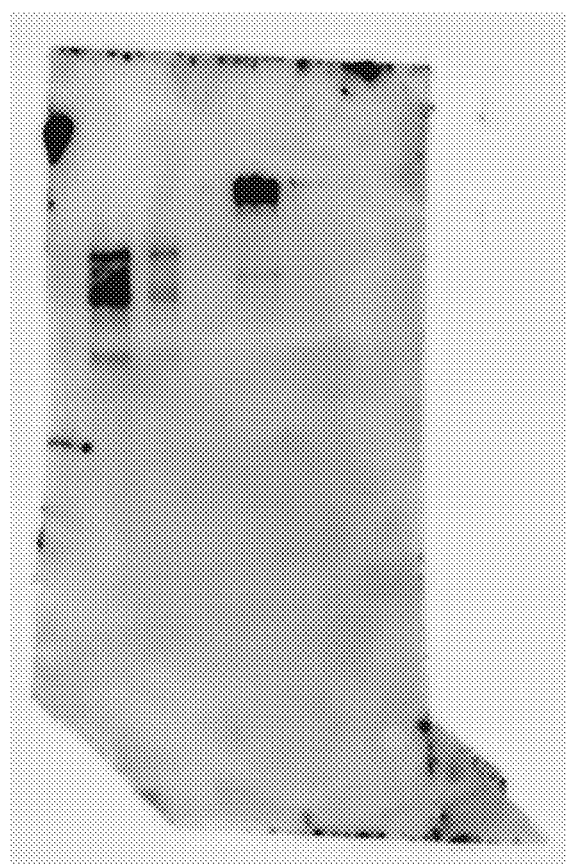
FIG. 7. Western blot of MCF7 (left 2 stained lanes) and MDS-L (right stained lane)

Then it was put in ECL Prime western blot reagent for 5 minutes without rocking, and put in an camera system and read for 10 minute Result:

The Western blot result is shown in FIG. 7. The left two lanes that have visible bands are MCF7 are and have 12 ug and 3 ug respectively of total protein loaded (Lanes 4 and 5). The right stained lane is MDS-L (lane 7) and by protein assay has 8 ug protein loaded. But by commassie staining of a gel run in parallel it appeared the MCF7 in lane 4 actually had about half as much protein as the MDS-L in lane 7. The stained IGF-1R band in MDS-L lane 7 runs above 200 kDa. The two stained bands in the MCF7 lanes run at about between 80 and 150 kDa. IGF-1R is a dimer of predicted molecular weight of 205 kD, where each monomer contains a 81 kDa and a 20 kDa polypeptide. So the MDS-L bands are consistent with a 205 kDa dimer and the MCF7 bands are consistent with the 81 kDa polypeptide and 102 kDa monomer.

MCF7 is the standard cell line for high expression of IGF-1R, and MDS-L has approximately the same amount of IGF-1R. So MDS-L has high expression of IGF-1R.

Example 15

IGF-MTX Inhibits Proliferation of Solid Tumor Prostate and Breast Cancer Cell Lines LNCaP and MCF7

In Vitro Proliferation Assays

LNCaP cells were plated in a 96-well plate at 5,000 cells per well in RPMI+glutamine+10% FCS medium in 1001. After 24 hours, 100 µl fresh medium was added containing no drug (control), IGF-MTX or MTX at the indicated concentration. After 48 hours of further incubation, cell proliferation was assayed with the Cell Counting Kit-8 (Dojindo Molecular Technologies, Kumamoto, Japan) according to the manufacturer's instructions.

MCF7 was cultured in Eagle's Minimum Essential Medium, with 0.01 mg/ml human recombinant insulin, 10% fetal bovine serum, and pen/strep. For in vitro proliferation assays it was plated at 8,000 cells per well in a 96-well plate. After 1 day 765IGF-MTX or MTX was added to the indicated concentration. After 5 more days, 1 uCi tritiated thymidine was added per well in 50 ul fresh medium. Six hours later the cells were harvested and radioactivity counted.

In Vitro Tumor Inhibition

To evaluate effects on cell proliferation, the IGF-MTX conjugate and free MTX were incubated with LNCaP tumor cells in vitro. Both agents inhibited proliferation of LNCaP cells compared to untreated control cells. At the highest tested concentration of 2000 nM, free MTX caused significantly greater inhibition than IGF-MTX (P=0.003). Inhibition of proliferation by free MTX at 500 nM did not differ significantly from that of IGF-MTX at 2000 nM. The $IC_{50}$ for longR3-IGF-MTX was about 1000 nEq/L (nM methotrexate groups) (McTavish, H. et al., Translational Research 2009; 153:275-282) In this case, the IGF portion of the conjugate was long-R3-IGF.

Figure 8:
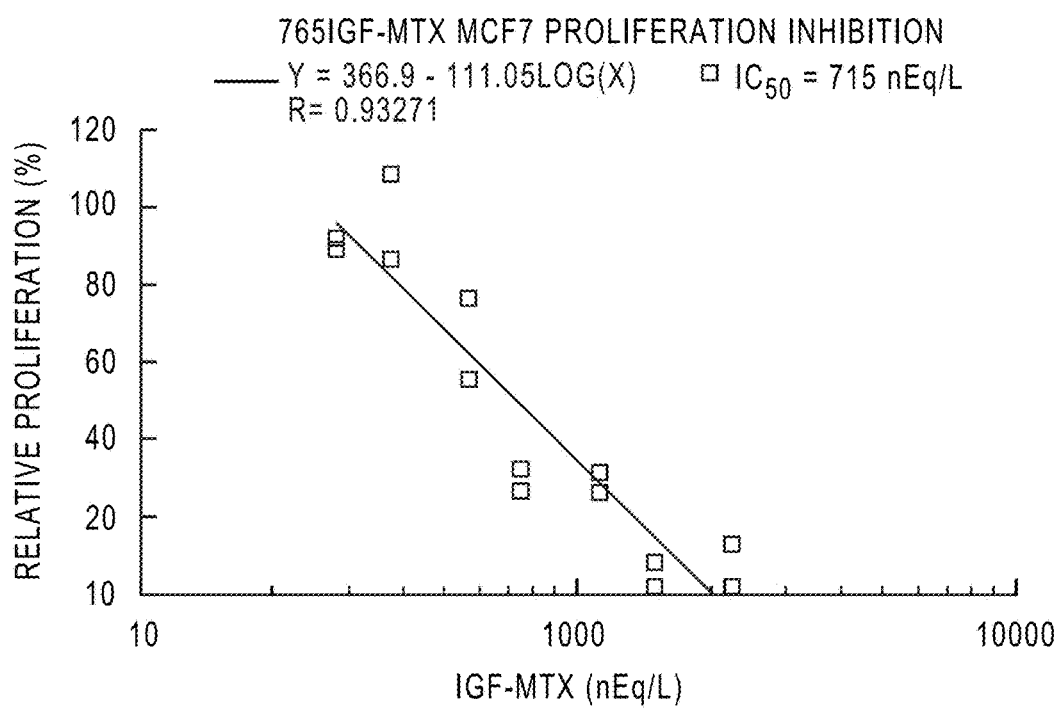
FIG. 8. Inhibition of proliferation of MCF7 cells by 765IGF-MTX.

The results of a proliferation assay of 765IGF-MTX with MCF7 cells is shown in FIG. 8. In this case, the IC50 of 765IGF-MTX was 715 nEq/ml (FIG. 8). The IC50 for free methotrexate against MCF7 in a parallel assay was 17 nM (data not shown).

Example 16

IGF-MTX Inhibits Tumor Growth In Vivo of a Prostate Cancer Cell Line in Mice at More Effectively than Free MTX, Even at a 6-Fold Lower Dose of IGF-MTX IGF-MTX Conjugate Synthesis, Analysis and Quantification Long-R3-IGF-1 was purchased from Novozymes GroPep (Novozymes BioPharma AU, Thebarton, Australia). MTX was purchased from Sigma (St. Louis, Mo., USA). Long-R3-IGF-1 (20 mg) was dissolved in 3.0 ml, 10 mM HCl. Sodium phosphate (2.5 ml, 200 mM, pH 7.4) and solid urea (1.625 g) were added to the solution. The solution was dialyzed (3500 m.w. cut-off) against 20 mM sodium phosphate, pH 7.4, 5 mM NaCl, 6.5 M urea (urea dialysis buffer) overnight at 4° C. MTX hydrate (14.8 mg) neutralized with 1.4 mole equivalents of NaOH dissolved in 0.4 ml urea dialysis buffer was added to the long-R3 IGF solution in the dialysis bag. Long-R3-IGF-1 and MTX were coupled by incubation with 1-ethyl-3-[3-dimethylaminopropyl]carbodiimide hydrochloride (EDC). EDC is a zero-length cross-linker that produces direct amide bonds between protein amine groups and the carboxyl group on MTX. EDC (60 mg) was freshly dissolved in urea dialysis buffer (0.6 ml) and then added to the dialysis bag, which was sealed and stored in a dish for 2 hours at room temperature. The reaction is schematically shown in FIG. 1.

After 2 hours, the bag was placed in urea dialysis buffer and dialyzed 3.5 hours at 4° C. The dialysis buffer was changed to 2 mM HCl, and dialysis was continued overnight. Long-R3-IGF-1 has 3 lysine residues and an amino terminal for a total of 4 amino groups available for conjugation. To determine the extent of saturation, the MTX concentration in the conjugated long-R3-IGF-1 protein was determined by optical absorption at pH 11 using $\epsilon_{372\ nm}$=6.47 mM$^{-1}$. The conjugated protein is hereafter referred to as IGF-MTX (for long-R3-IGF-1-methotrexate).

In Vivo Tumor Growth Assays

MCF7 cells (human breast adenocarcinoma cell line) were grown in Eagle's minimal essential medium supplemented with 0.1 mg/ml insulin and 10% FCS. The estrogen-dependent MCF7-L cell line was a gift from Deepali Sachdev of the University of Minnesota. MCF7-L cells were grown in modified IMEM medium (Invitrogen, Carlsbad, Calif., USA) supplemented with 0.1 mg/ml insulin. LNCaP cells (metastatic human prostatic adenocarcinoma) were grown in RPMI supplemented with glutamine and 10% FCS (Invitrogen, Carlsbad, Calif., USA). Cells were grown at 37° C. in a 5% $CO_2$ humidified atmosphere. In each case, cells were grown to approximately two-thirds confluence, harvested by trypsinization, washed with rich medium and then washed twice with PBS and resuspended in phosphate buffered saline in BD matrigel matrix (Becton Dickinson, Franklin Lakes, N.J., USA). Cells were injected intradermally in mice on the back. An estrogen pellet (0.5 mg estradiol, 60-day release, Innovative Research of America, Sarasota, Fla., USA) was implanted subcutaneously between the shoulder blades two days before implanting MCF7 and MCF7-L cells. MCF7 and MCF7-L cells were implanted in 8-week-old female nu/nu mice. LNCaP cells were implanted in 8-week-old male nu/nu mice. The IGF-MTX conjugate was administered in 2 mM HCl, 1% glycerol. MTX was dissolved in PBS. Untreated vehicle controls received 2 mM HCl, 1% glycerol. Drug was administered intravenously by tail-vein injection in a volume of 12.5:1 per gram mouse weight. All studies were approved by the University of Minnesota Animal Care and Use Committee and conformed to relevant ethical guidelines.

Results: Xenograft Tumor Growth Inhibition in Mice

Figure 9:
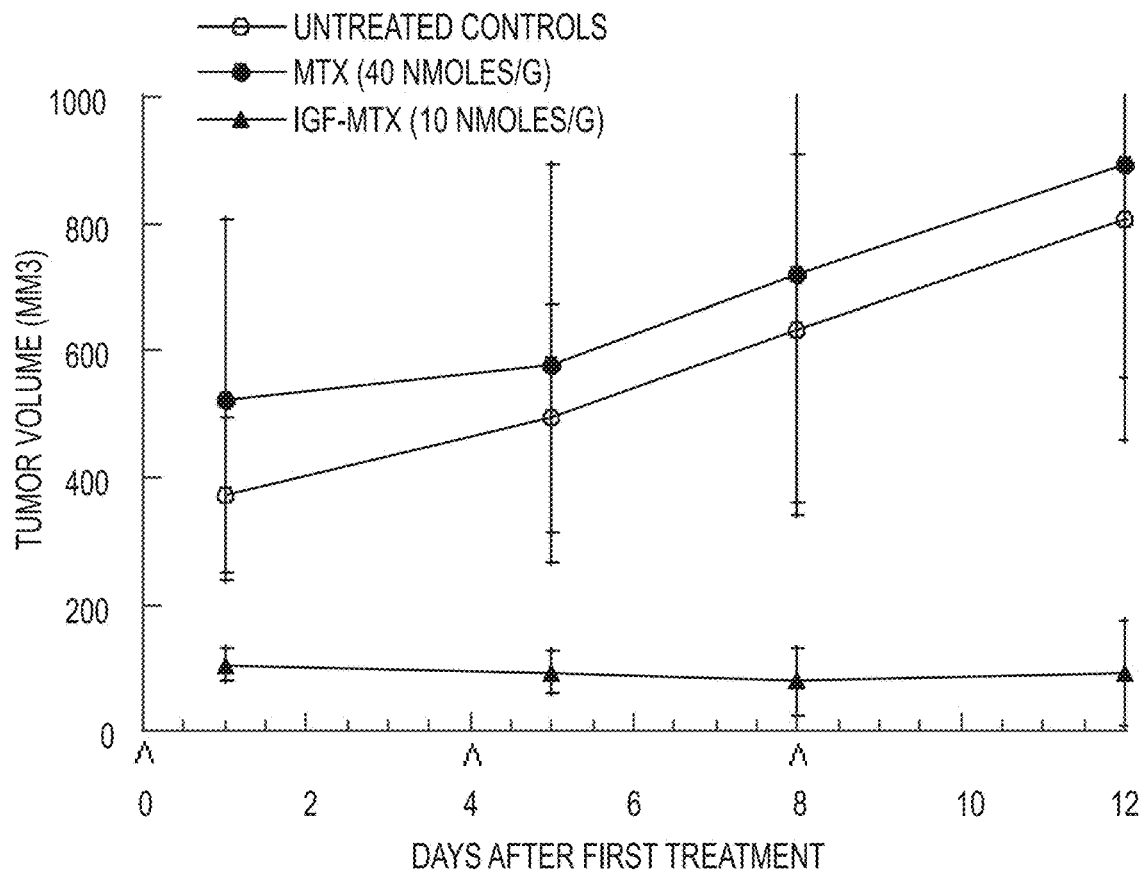
FIG. 9. In vivo tumor growth inhibition by IGF-MTX and free MTX of MCF7 tumors in nu/nu mice.

Three in vivo studies were performed to assess the targeting of MTX with long-R3-IGF-1. In the initial preliminary study, breast cancer MCF7 cells were implanted intradermally in the backs of nude mice. When tumors in 15 mice became palpable (approximately 5×5 mm), the mice were randomly distributed into three groups (n=5 per group). After randomization, mice were treated on days 0, 4 and 8 with intravenous tail vein injection of vehicle, free MTX at 40 nmol/g or IGF-MTX at 10 nmol of MTX/g. Even by one day after the first treatment, tumors in the IGF-MTX conjugate-treated group were smaller than those in the other groups (FIG. 9). For the 12 days of observation, tumors continued to grow in the free MTX and untreated control groups, whereas tumors treated with IGF-MTX showed no signs of tumor growth on average. There was approximately an 8-fold difference in tumor volume on average between the IGF-MTX conjugate-treated group and the MTX-treated group at day 12, which was found to be statistically significant (P=0.048, unpaired t test). The tumor volume in mice treated with the IGF-MTX conjugate was lower even though the conjugate was used at a 4-fold lower dose of MTX than the dose of free MTX. These data indicate that the IGF-MTX conjugate is more effective than free MTX at controlling the growth of MCF7 tumors in vivo even when used at a quarter of the dose.

Figure 10:
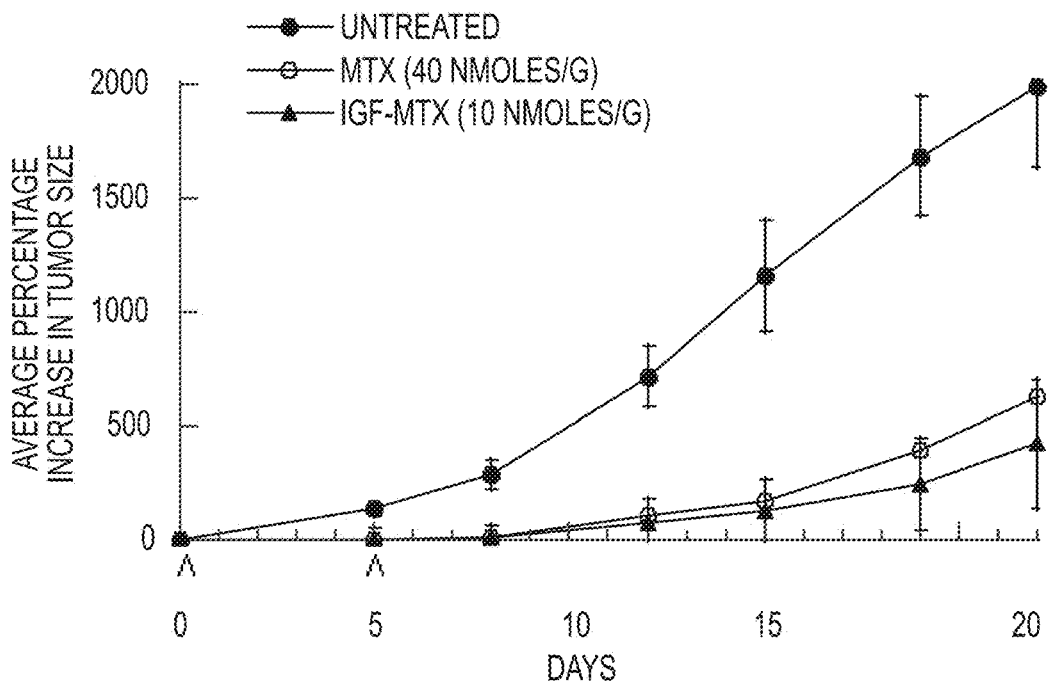
FIG. 10. In vivo tumor growth inhibition by IGF-MTX and free MTX of MCF7-L tumors in nu/nu mice.

The second in vivo study was conducted using an estrogen-dependent MCF7 strain, MCF7-L. Tumor cells were implanted, and mice were monitored for tumor growth. Nine days after tumor implantation, 15 mice with visible tumors were sorted into three groups with equal average tumor size. Mice were then injected by tail vein on days 0 and 5 with vehicle, free MTX (40 nmol/g) or the IGF-MTX conjugate (10 nmol of MTX/g). Tumor growth was inhibited about equally in animals treated with IGF-MTX or free MTX at day 22 (FIG. 10). However, the dose of IGF-MTX conjugate was 4-fold lower than the dose of free MTX. The difference in tumor volume at day 22 between the IGF-MTX group and untreated controls was significant (P=0.008). These data again suggest that a lower dose of IGF-MTX is equally effective as higher doses of free MTX at inhibiting tumor growth in vivo.

Figure 11:
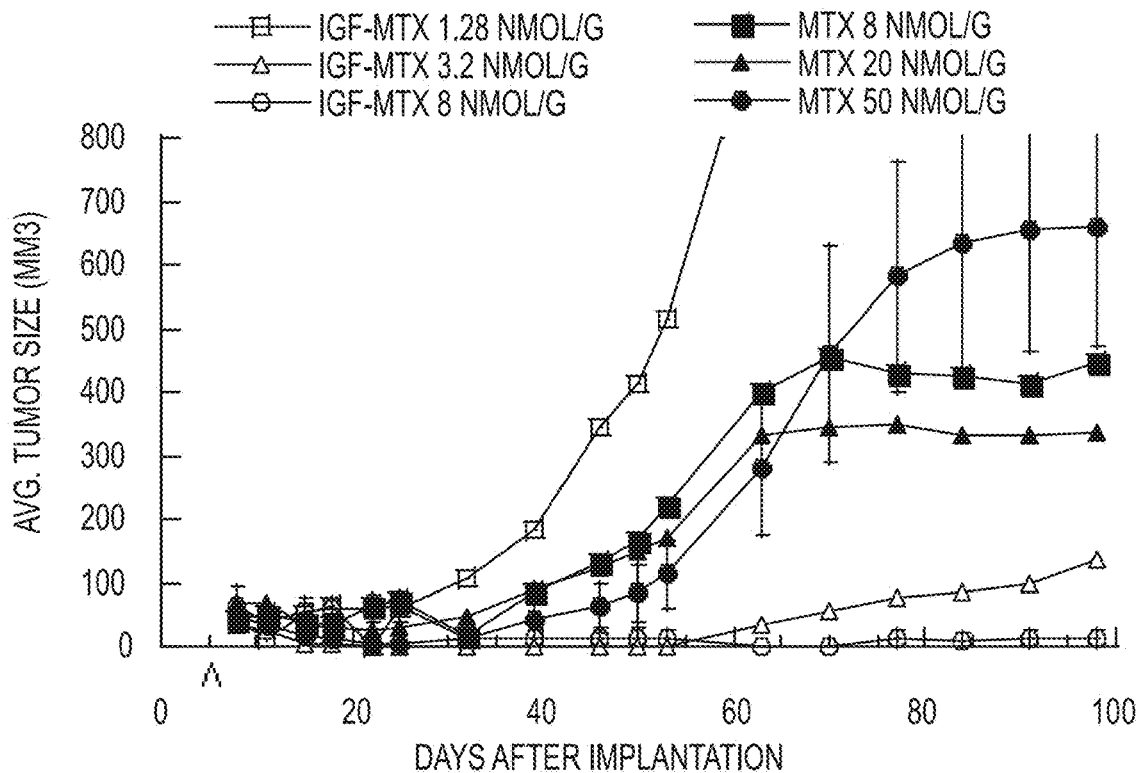
FIG. 11. In vivo tumor growth inhibition by IGF-MTX and free MTX of LNCaP tumors in nu/nu mice.

In a final in vivo study, prostate cancer LNCaP cells were implanted intradermally on day 0 in mice, which were then randomized to different treatment groups. Mice received a single tail vein injection on day 5 (before tumors were visible) with MTX or the IGF-MTX conjugate at various concentrations (FIG. 11). Tumor size was much smaller in the groups treated with 8 nmol/g or 3.2 nmol/g of the IGF-MTX conjugate (dosage expressed as moles of each MTX molecule) compared to mice treated with higher doses of free MTX (50, 20 or 8 nmol/g). The lowest dose of IGF-MTX conjugate tested, 1.28 nmol/g, did not inhibit tumor growth. The difference in tumor growth in animals receiving 8 nmol/g of IGF-MTX compared to 50 nmol/g of free MTX at the conclusion of the study (day 98) was significant (P=0.04, two-tailed t test). There was also a significant difference between the pooled results for the two highest IGF-MTX concentrations (8 nmol/g and 3.2 nmol/g) and the highest free MTX concentration (50 nmol/g) (P=0.011). In addition, the difference between the pooled results for two highest IGF-MTX concentrations (8 nmol/g and 3.2 nmol/g) and free MTX concentrations (20 nmol/g and 50 nmol/g) was significant (P=0.029). Based on these data, it is reasonable to conclude that the IGF-MTX conjugate was more effective than free MTX against tumor growth in vivo, even at a 6.25-fold lower dose (8 nmol/g IGF-MTX vs. 50 nmol/g MTX).

Discussion:

IGF-MTX (LR3IGF-MTX) was at least 6-fold more effective than free MTX in inhibiting tumor growth in the LNCaP model in the sense that a 6-fold lower molar dose of methotrexate groups in IGF-MTX (8 nEq/kg) was more effective than the 6-fold higher molar dose of free MTX (50 nmoles/kg). Likewise, in the MCF7 models IGF-MTX was at least as effective as free MTX even at a 4-fold lower molar dose of IGF-MTX than free MTX. This contrasts with in vitro results, where with MCF-7 cells the IC50 of MTX is about 50-fold lower than IGF-MTX (17 nM MTX versus 715 nEq/L for IGF-MTX). This indicates there is tremendous targeting of the IGF-MTX to the tumor cells in vivo.

Example 17

Flow Cytometry of Blood Cells and MDS-L Show Health Blood Cells have Almost No CD34 or IGF-1R and MDS-L Cells have High Levels of CD34 and IGF-1R A flow cytometry assay was developed to test for CD34, a marker of blood stem cells, and IGF-1R. The IGF-1R (referred to as CD221) was detected with CD221 clone 1H7 from BD Biosciences.

Flow cytometry was done on hemolyzed whole blood from healthy donors and the blood mixed with varying volumes of 1 million/ml MDS-L cells that were viably frozen.

Figure 12:
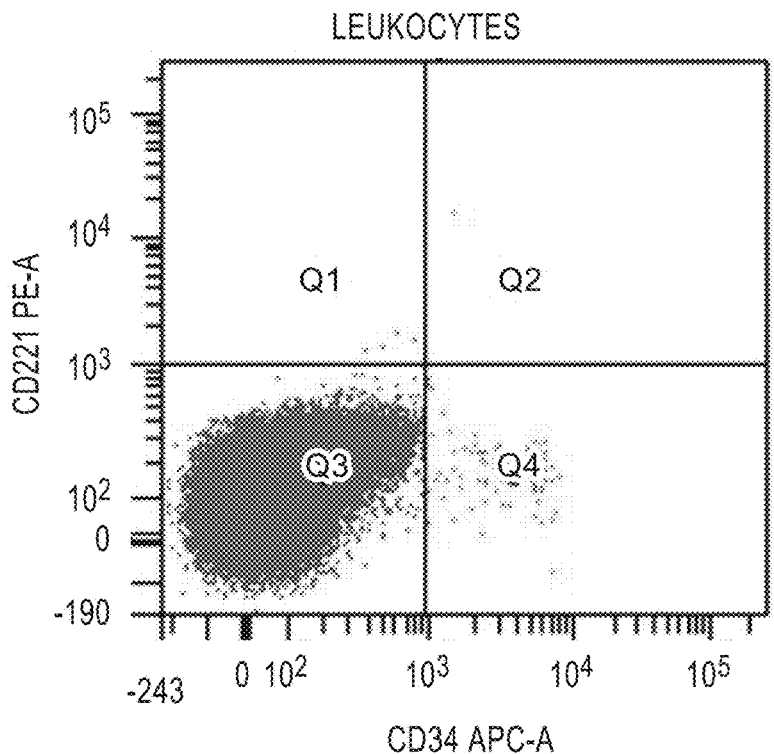
FIG. 12. Flow cytometry of hemolyzed blood from a healthy volunteer detecting CD34 and IGF1R (CD221).
Figure 13:
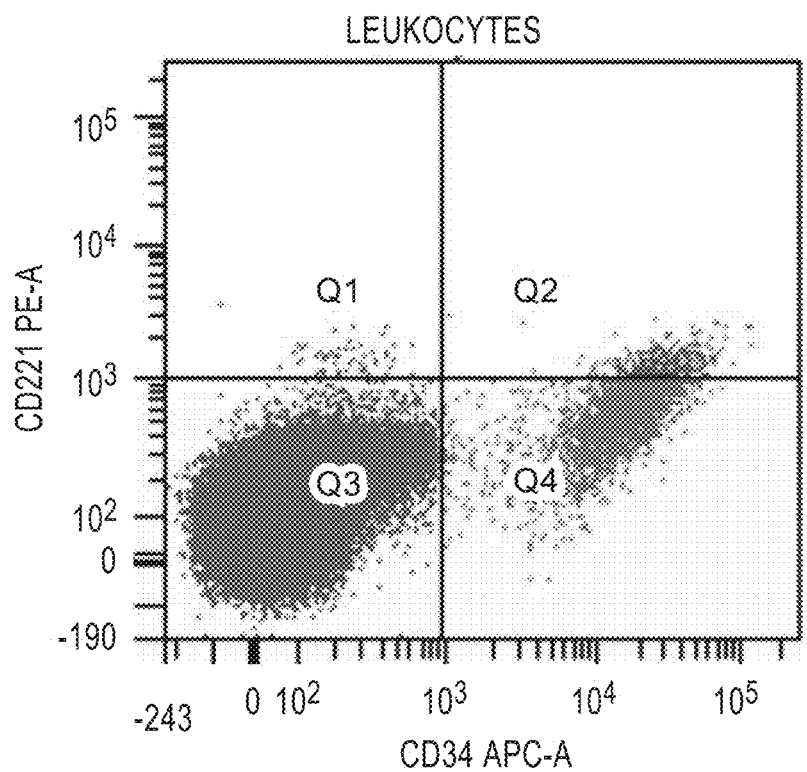
FIG. 13. Flow cytometry of hemolyzed blood from a healthy volunteer (100 ul) mixed with 10 ul of 1 million/ml MDS-L cells detecting CD34 and IGF1R (CD221).
Figure 14:
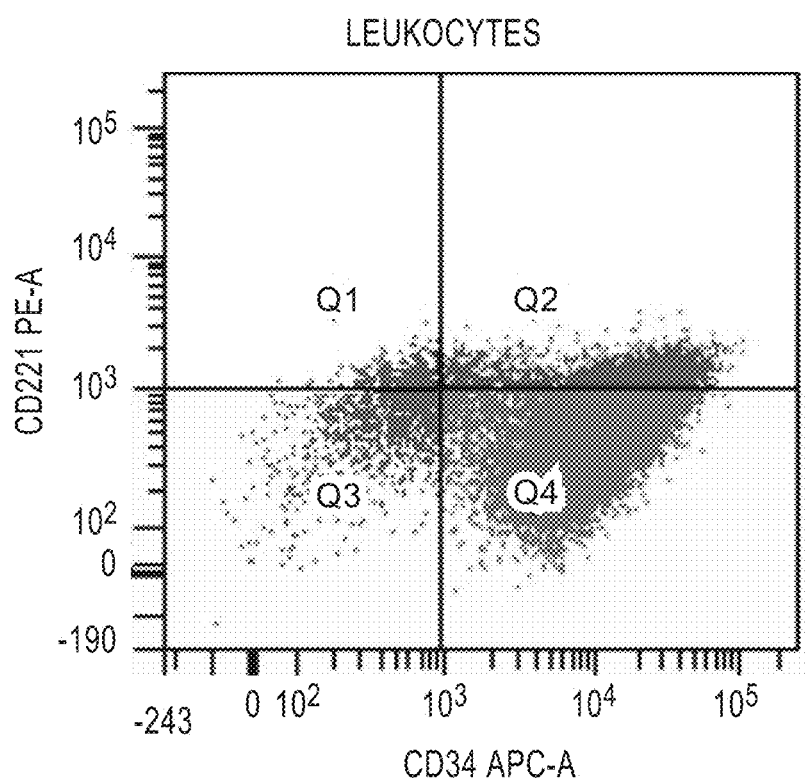
FIG. 14. Flow cytometry of MDS-L cells (1 million/ml) detecting CD34 and IGF1R (CD221).

The results from whole blood alone is shown in FIG. 12, from 100 ul whole blood mixed with 10 ul MDS-L cells in FIG. 13, and the result with 75 ul of MDS-L cells alone in FIG. 14. The percentage of cells in Q1 (CD221+/CD34−), Q2 (CD221+/CD34+), and Q4 (CD221−/CD34+) are summarized in Table 2.

TABLE 2

|  | 100 ul hemolyzed blood, with | | | MDSL cells |
|---|---|---|---|---|
|  | 0 uL MDSL | 10 uL MDSL | 50 uL MDSL | only 75 uL |
| Q1 % Parent (CD221+/CD34−) | 0 | 0.1 | 0.3 | 0.7 |
| Q2 % Parent (CD221+/CD34+) | 0 | 0.4 | 1.8 | 9.9 |
| Q4 % Parent (CD221−/CD34+) | 0.1 | 2.6 | 12.5 | 86.9 |

In a healthy donor's blood, almost no leukocytes were positive for either CD34 or IGF1R (CD221). In MDS-L cells, almost all cells were positive for either CD34 or IGF1R, and 9.9% were positive for both. This suggests MDS cells are almost the only cells in blood positive for IGF1R or for CD34 or for both.

Example 18

AML-03: Pilot Study of IGF-Methotrexate Conjugate in the Treatment of Myelodysplastic Syndrome, CMML and Oligoblastic AML Synopsis Primary Objective:

The primary objective of this study is to determine the safety and tolerability of utilizing the insulin-like growth factor-1-methotrexate conjugate, 765IGF-MTX for the treatment of advanced, previously treated myelodysplastic syndrome (MDS), chronic myelomonocytic leukemia (CMML) and oligoblastic acute myelogenous leukemia (oligoblastic AML or O-AML), including determining the maximum tolerated dose (MTD).

Secondary Objective:

The secondary objective of this study is to determine the clinical benefit of 765IGF-MTX as measured by response rate, progression-free survival, and overall survival in patients with advanced, previously treated MDS, CMML, or O-AML.

Patient Population:

Diagnosis of MDS, CMML or O-AML that is refractory to or intolerant of standard therapy and is no longer likely to respond to such therapy Patient must have recovered from the acute toxic effects (≤grade 1 CTCAE v.4.0) of previous anti-cancer treatment prior to study enrollment Age 18 years or older ECOG performance status 0, 1, or 2 (appendix III)

Study Design:

This pilot study will evaluate use of IGF-Methotrexate conjugate (765IGF-MTX) in patients with advanced, previously treated MDS, CMML and O-AML. 765IGF-MTX at a dose of 0.20 to 2.5 μequivalents per kg is administered as an IV infusion over 1.5 hours on days 1, 8 and 15 of a 28 day cycle. Treatment continues until disease progression, as assessed after 2 cycles, unacceptable toxicity, or patient refusal. Assessment of response will be confirmed by bone marrow studies performed at the end of cycles 2, 4, and 6 (each +/−3 days).

Once a final maximum tolerated dose level (MTD) is determined, the pharmacokinetics (PK) of 765IGF-MTX will be assessed on days 1 and 2 and days 15 and 16 of cycle 1 at the MTD in three patients.

Study Schema

Patients are screened, and then if entered into the trial treated on days 1, 8, and 15 of a 28-day cycle. Patients are treated until disease progression, unacceptable toxicity, or patient elects withdrawal. Bone marrow samples are taken within 28 days before the first dose, and after cycles 2, 4, and 6. Pharmacodynamic samples are taken on day 1 of cycle 1, days 1 and 15 of cycle 2, and day 15 of subsequent cycles. At the maximum tolerated dose, pharmackonetic samples are taken over 2 days on days 1-2 and days 15-16 of cycle 1.

Phase I Dose Levels

| Dose Level | 765IGF-MTX Dose | Number of Patients* |
|---|---|---|
| 1 | 0.20 μequivalents per kg | 1-9 |
| 2 | 0.40 μequivalents per kg | 1-9 |
| 3 | 0.80 μequivalents per kg | 1-9 |
| 4 | 1.6 μequivalents per kg | 1-9 |
| 5 | 2.5 μequivalents per kg | 1-9 |

*dose escalation cohorts between 1-9 patients; total of 9 patients in MTD cohort. At the discretion of the principal investigator, intra-patient dose escalation between cycles is also allowed.

1. Objectives 1.1. Primary Objective

The primary objective is to determine the safety and tolerability of 765IGF-MTX when used for the treatment of advanced, previously treated MDS, CMML or O-AML, including determining the MTD of IGF-MTX.

1.2. Secondary Objectives 2.2.1 Evaluate clinical benefit of 765IGF-MTX by evaluating the overall response rate (ORR; =CR and PR), progression-free survival (PFS), cumulative incidence of progression (CIP), and overall survival (OS) in patients with advanced, previously treated O-AML, CMML or MDS.

1.3. Correlative Objectives 1.3.1. Characterize pharmacokinetics (PK) of 765IGF-MTX, 765IGF, methotrexate, and 7-OH methotrexate 1.3.2. Assess potential for QT prolongation 1.3.3. Assess Pharmacodynamic (PD) effects of 765IGF-MTX on soluble IGF-1 and IGF-1R levels 1.3.4. Assess formation of antibodies against 765IGF-MTX 1.3.5. Assess formation of neutralizing antibodies 1.3.6. Assess level of diseased cell IGF-1R expression 2. Endpoints
   2.1. Primary Endpoint
   The primary endpoint is safety and tolerability of 765IGF-MTX. This will be assessed by evaluation of adverse effects (AEs) as defined by CTCAE v.4.0.
   2.2. Secondary Endpoints
   2.2.1. Evaluate clinical benefit of 765IGF-MTX by assessment of ORR, PFS, CIP, OS.
   2.2.2. Complete remission (CR), CRi, PR as defined by the following response criteria for hematologic malignancies (see Appendix I Tables 5 and 6, and Appendix II):
      2.2.2.1. Acute leukemia: 2015 SWOG Manual Chapter 11A[44] (Appendix I); European LeukemiaNet criteria[45] and 2003 IWG criteria[46]
      2.2.2.2. MDS: 2006 IWG criteria[47] (Appendix II)
   2.3. Correlative Endpoints
      3.3.1 Pharmacokinetic (PK) parameters as defined by AUC from start of infusion to time of last quantifiable plasma concentration, AUC from start of infusion to infinity, maximum observed plasma concentration, time of maximum plasma concentration, terminal elimination constant of both free MTX and IGF-MTX for 765IGF-MTX, 765IGF, methotrexate, and 7-OH methotrexate.
      3.3.2 Evaluation of potential of 765IGF-MTX for QT prolongation
      3.3.3 Pharmacodynamic parameters (PD) as defined here by plasma IGF-1 and plasma IGF-1R concentration, and standard of care systemic PD variables (cell count, differential)
      3.3.4 Plasma 765IGF Level and 765IGF-MTX toxicity/response
      3.3.5 Serum and blood IGF-1R level and 765IGF-MTX Toxicity/Response
      3.3.6 Assess formation of antibodies against 765IGF-MTX
      3.3.7 Assess formation of neutralizing antibodies
      3.3.8 IGF-1R expression level in diseased tissue in bone marrow, as measured by IHC, and flow cytometry, and in blood cells as measured by flow cytometry.

3. Overall Design and Study Plan

This pilot study will evaluate the safety and clinical benefit of 765IGF-MTX in patients with advanced, previously treated MDS, CMML or O-AML. 765IGF-MTX is administered as an IV infusion over 1.5 hours on days 1, 8 and 15 of a 28 day cycle. Treatment continues until disease progression, unacceptable toxicity, or patient refusal. Assessment of response will be confirmed with bone marrow studies performed at the end of cycle 2, and every 8 weeks+/−7 days (2 cycles) thereafter up to the end of cycle 6, and at physician's discretion thereafter.

Dose Finding Component: Up to 5 dose levels will be tested (refer to schema on page 6). The maximum tolerated dose (MTD) will be determined using the modified toxicity probability interval design with dose limiting toxicity (DLT) estimated at 0.33.

Our modification involves using cohorts of size 1 for the initial doses, which allows rapid escalation through the initial dose levels, and expanding to cohorts of size 3 once any grade 2 or higher toxicity is observed that is considered related to study drug (with the exception of alopecia, nausea, or diarrhea). Additional patient cohorts will not be enrolled until 1 of 1 (with no grade 2 toxicity), 3 of 3, 5 of 6, or 7 of 9 patients at the current dose level complete all planned treatment for cycle 1 (defined as 3 doses of 765IGF-MTX without DLT and are able to start cycle 2 with no more than a 2 week delay. At the discretion of the principal investigator, intra-patient dose escalation between cycles is also allowed but only after 2 cycles at one dose level, and patients who were intra-patient dose escalated cannot be the only patients treated at the higher dose level.

Dose escalation will be done based on the modified toxicity probability interval design found and after consultation with the study statistician. If none of the dose levels are acceptable at study completion, an optimal dose level will not be identified and the drug does not warrant further investigation.

Maximum Tolerated Dose (MTD) Cohort with pharmacokinetics (PKs) and pharmacodynamics (PD): The MTD will be defined as the highest dose associated with DLT in less than or equal to 33% of patients treated. Once the MTD is determined, enrollment will continue until 9 patients total are accrued at the MTD. For this group, pharmacokinetics will be performed on at least 3 patients before and for up to 48 hours after drug administration on days 1 and 15 of cycle 1. Pharmacodynamic samples will be assessed on day 1 of cycle 1, and days 1 and 15 of cycle 2 before the infusion of 756IGF-MTX, and one sample will also be drawn within the fourth week of each treatment cycle.

If none of the dose levels are acceptable at study completion, an optimal dose level will not be identified and the drug does not warrant further investigation.

Dose limiting toxicity (DLT) for a patient is defined as one of the following events occurring during cycle 1:
   Grade 4 or greater treatment related hematologic toxicity for >7 days during the first cycle (28 days) of therapy
   Grade 3 or greater treatment related clinical non-hematological toxicity (excluding ≥grade 3 nausea, vomiting, or diarrhea without maximal medical intervention and/or prophylaxis) during the first cycle (28 days) of therapy
   Febrile neutropenia during the first cycle (28 days) of therapy
   Platelets less than $10 \times 10^9$/L with clinically significant bleeding during the first cycle (28 days) of therapy Additional patient cohorts will not be enrolled until 1 of 1 (with no grade 2 toxicity), 3 of 3, 5 of 6, or 7 of 9 patients at the current dose level complete all planned treatment for cycle 1 (defined as 3 doses of 765IGF-MTX without DLT and are able to start cycle 2 with no more than a 2 week delay.

The MTD will be defined as a dose level at which fewer than 33% of patients treated experience a DLT.

A minimum of 9 patients are to be treated at the MTD to assure safety and 765IGF-MTX based pharmacokinetics will be performed on at least 3 patients in total.

Pharmacokinetics will be performed before and for up to 24 hours after drug administration on days 1 (for 24 hrs) and 15 (for 24 hrs) of cycle 1. Pharmacodynamic samples will be assessed pre-dosing on day 1 of cycle 1, pre-dosing on days 1 and 15 of cycle 2, and pre-dosing on day 15 of all subsequent cycles.

4. Selection of Patients

Study entry is open to adults ≥18 years regardless of gender or ethnic background. While there will be every effort to seek out and include women and minorities, the patient population is expected to be no different than that of other studies performed at the Mayo Clinic.

4.1. Inclusion Criteria
5.1.1 Diagnosis of O-AML that is refractory to or intolerant to standard therapy and is no longer likely to respond to such therapy (at least one line of therapy); or
Diagnosis of MDS/CMML that is refractory to or intolerant to standard therapy and is no longer likely to respond to such therapy (at least one line of therapy)
5.1.2 Confirmed histologic diagnosis on bone marrow biopsy and aspirate within 14 days of trial entry prior to starting cycle 1.
5.1.3 Platelets>10×10$^9$/L
5.1.4 Age≥18 years
5.1.5 ECOG performance status of 0, 1 or 2 (appendix III).
5.1.6 Prior systemic chemotherapy, immunotherapy, or biological therapy, radiation therapy and/or surgery are allowed; prior use of systemic methotrexate >1 month prior to study entry is allowed. Intrathecal methotrexate is allowed prior to and during treatment per investigator discretion.
Time since prior therapy and the first dose of study drug:
At least 2 weeks since prior radiation, non cytotoxic small molecule drugs, prior major surgery (defined as a surgery involving a risk to the life of the patient; specifically: an operation upon an organ within the cranium, chest, abdomen, or pelvic cavity), prior systemic FDA-approved therapy
5.1.7 Patient must have recovered from the acute toxic effects (≤grade 1 CTCAE v.4.0) of previous anti-cancer treatment prior to study enrollment; the only exception is that grade 2 neuropathy is permitted 5.1.8 Adequate organ function within 14 days of study registration defined as:

| System | Laboratory Values |
|---|---|
| Hematologic | |
| Platelets | >10 × 10$^9$/L |
| Hepatic | |
| Bilirubin total | ≤1.5 × ULN |
| Alkaline Phosphatase, AST and ALT | ≤3 × ULN (<5 × ULN is acceptable if liver has tumor involvement) |
| Renal | |
| Serum Creatinine, or | ≤1.5 × ULN |
| Creatinine Clearance, or | ≥60 mL/min |
| GFR, or | ≥60 mL/min |
| 24 hour urine creatinine clearance | >50 mL/min |

5.1.9 Negative urine or serum pregnancy test in females. Male and female patients with reproductive potential must use an approved contraceptive method if appropriate (for example, abstinence, oral contraceptives, implantable hormonal contraceptives, or double barrier methods) during, and for 3 months after the last dose of 765IGF-MTX.
5.1.10 Voluntary written informed consent before performance of any study-related procedure not part of normal medical care, with the understanding that consent may be withdrawn by the patient at any time without prejudice to future medical care.
6. Study Parameters
6.1 Standard of Care Procedures

| | Baseline, within 28 days of enrollment | Each treatment cycle$^a$ | | | Every 8 weeks (±1 week) | 30 days (±1 week) after final dose of 765IGF-MTX[1] |
|---|---|---|---|---|---|---|
| | | Day 1[2] (±1 day) | Day 8 (±1 day) | Day 15 (±1 day) | | |
| Signed consent (Registration/Enrollment must occur within 30 days. | x | | | | | |
| Medical history | x | X | | | | X |
| Review of prior therapy | x | | | | | |
| Bone marrow biopsy and aspirate confirming disease and blast count[3] | x | | | | x[3] | |
| Physical exam | x | X | | | | X |
| Vital signs | x | X | x | x | | X |
| Height, weight | x | X | | | | X |
| Concomitant meds review | x | X | x | x | | X |
| Performance status | x | X | | | | X |
| Symptom and toxicity | x | X | x | x | | x[3] |
| CBC w/diff[4] | x | X | x | x | | X |
| CMP (with: calcium, glucose, sodium, potassium, CO2, chloride, BUN, creatinine, albumin, ALT, AST, bilirubin, alkaline phosphatase, total protein)[4] | x | x | | x | | X |

|  | Baseline, within 28 days of enrollment | Each treatment cycle[a] Day 1[2] (±1 day) | Day 8 (±1 day) | Day 15 (±1 day) | Every 8 weeks (±1 week) | 30 days (±1 week) after final dose of 765IGF-MTX[1] |
|---|---|---|---|---|---|---|
| Uric acid (cycle 1 only) | x | x |  | x |  |  |
| LDH | x | x |  |  |  |  |
| UA for protein | x[5] | x |  |  |  | x |
| HbA1C for diabetic patients | x |  |  |  |  | x |
| Serum pregnancy test for females of child-bearing potential | x |  |  |  |  |  |
| ECG[6] | x | x |  |  |  | x |
| 765IGF-MTX administration |  | x | x | x |  |  |

[a]Subsequent cycles beyond cycle 1 must meet the criteria found in section 7.3 and may begin 1 day earlier or up to 2 days later to accommodate scheduling issues.
[1]For patients who leave treatment with a response, repeat appropriate disease assessment every 6-12 weeks until progression or start of a new treatment.
[2]For cycle 1 only, tests and procedures do not need to be repeated if done within 3 days of day 1.
[3]Bone marrow biopsy should be at end of end of cycle 2, and every 2 cycles thereafter to cycle 6. Patients who achieve response (CR) could have repeat bone marrow biopsies per MD discretion.
[4]CBC and complete metabolic panel (CMP) will be performed weekly, or more frequently, as clinically necessary.
[5]Within 1 week of study enrollment. If urinalysis is abnormal then a 24-hour urine for protein must demonstrate ≤1 gm protein in 24 hours to allow participation in the study
[6]ECG performed only in cycle 1 and at the end of study visit 30 days after the final dose.

6.2 Research Related Procedures

|  | Baseline (within 28 days of Cycle 1, D 1 | C1D 1 | C1 D 15 | C2 D 1 | C2 D 15 | Every 8 weeks (±1 week) up to week 24 | Cycles 4 and 6, D 15 |
|---|---|---|---|---|---|---|---|
| PKs per section 9.1 |  | x[1] | x[1] |  |  |  |  |
| ECG (QT study) done during PK blood collection per section 9.3. PK patients only.[2] |  | x[2] | x[2] |  |  |  |  |
| Serum IGF-1 level. All subjects. |  | x[3] |  | x[3] | x[3] |  | x[3] |
| Serum and blood IGF-1R level. All subjects. |  | x[3] |  | x[3] | x[3] |  | x[3] |
| Anti-765IGF-MTX antibody assay. All subjects. |  | x[3] |  | x[3] | x[3] |  | x[3] |
| Neutralizing antibodies. All subjects. |  | x[3] |  | x[3] | x[3] |  | x[3] |
| IGF-1R expression in bone marrow biopsy and aspirate by IHC and flow cytometry. All subjects. | x[4] |  |  |  |  | x[4] |  |

| | Baseline (within 28 days of Cycle 1, D 1 | C1D 1 | C1 D 15 | C2 D 1 | C2 D 15 | Every 8 weeks (±1 week) up to week 24 | Cycles 4 and 6, D 15 |
|---|---|---|---|---|---|---|---|
| IGF-1R expression in blood cells by flow cytometry. All subjects. | x[5] | | | | | x[5] | |

[1] Done only in the PK patients in the MTD. Pre-765IGF-MTX infusion (at the time of am labs if am labs are within one hour of 765IGF-MTX infusion), 5 min before the infusion ends (+/−5 minutes), and at the following time points after completion of the infusion: 30 min (+/−5 minutes), 60 min (+/−15 minutes), 2 h (+/−15 minutes), 4 h (+/−15 minutes), 6 h (+/−15 minutes), 10 h (+/−15 minutes and 24 h (+/−2 hours)). The 10 hour time point will be collected on day 1 but not on day 15.
[2] Done only in PK patients in the MTD. Pre-765IGF-MTX infusion(+/−5 minutes), and 30 min (+/−5 minutes) after starting the infusion, at the following time points after completion of the infusion: 60 min (+/−15 minutes) and 3 hours (+/−15 minutes). In all patients, ECG is done at baseline, on day 1, cycle 1 (before the infusion), and 30 days (±1 week) after the final dose (see section 8.1).
[3] Blood draw prior to infusion
[4] Bone marrow biopsy and aspirate will be collected at baseline and every 8 weeks (±1 week) up to week 24, i.e., after cycles 2, 4, and 6, before the first dose of the next cycle. If no bone marrow aspirate viably frozen or freshly collected for flow cytometry is available from a patient in the 28-day baseline period before cycle 1, day 1, the patient may still enroll and no new bone marrow aspirate will be required for a baseline sample.
[5] Whole blood collection in EDTA tubes.

7. Correlative Studies

Information on the collection of blood samples for the correlative studies (collection tubes to be used, volume of blood drawn, collection processing, aliquot procedure and storage, and particular assay to be used) can be found in Appendix VII.

7.1 Pharmacokinetics 7.1.1 Pharmacokinetic Sample Collection

The pharmacokinetics of 765IGF-MTX will be examined following the doses administered on days 1 and 15 of cycle 1. On these days the 765IGF-Methotrexate will be infused in the morning as described in section 7.1.1. The research team will record the start and stop times of the infusion and volume of the 765IGF-MTX solution infused. Whole blood (6 mL) will be collected from an inserted butterfly needle on the opposite arm or from a peripheral site if the patient has a central venous catheter immediately prior to the 765IGF-MTX infusion, 5 min before the infusion ends, and at the following time points after completion of the infusion: 30 min, 60 min, 2 h, 4 h, 6 h, 10 h, and 24 h, (windows as above [Research-Related Procedures table, footnote 1). The 10 h time point will be collected on day 1 but not day 15. IGF-MTX and MTX unbound to IGF toxicokinetic analysis will be performed. These time points are based on pharmacokinetics in dogs. Please see Appendix VII for PK sample collection procedures.

7.1.2 Pharmacokinetic Sample Processing

Blood samples (6 mL) will be collected in 6-mL EDTA (purple top) tubes. The tube should be gently inverted a few times for complete mixing with the anticoagulant. The exact time of sample collection should be recorded on the tube label and Pharmacokinetics Data Form provided. The tube should be kept on wet ice until centrifugation. Within 120 minutes of blood collection, centrifuge each blood sample at approximately 3,000×g for 5-10 minutes at 4° C. Aliquots, approximately 0.5 mL each, will be pipetted into 4 separate plastic centrifuge tubes and frozen at −80° C. until analysis. Please see Appendix VII for PK sample collection procedures.

765IGF-MTX, 765IGF, methotrexate and 7-OH-methotrexate plasma concentrations will be determined using validated assays under GLP conditions at the Toxicology Research Laboratory, University of Illinois at Chicago.

7.1.3 Pharmacokinetic Parameter Determination

The pharmacokinetics of the 765IGF-Methotrexate, 765IGF, methotrexate and 7-OH methotrexate will be analyzed by compartmental and noncompartment approaches. Non-compartmental analysis of the plasma concentration-time data for each of the compounds of interest will be performed using WinNonlin 6.3 (Pharsight, St Louis, Mo.). Pharmacokinetic parameters to be estimated include: 1). area under the drug plasma concentration-time curve from the start of the infusion to the time of the last quantifiable plasma concentration ($AUC_{0-t}$), 2) AUC from the start of the infusion to infinity ($AUC_{0-\infty}$), 3). maximum observed plasma concentration ($C_{max}$), 4). time of maximum plasma concentration ($T_{max}$) and 5). terminal elimination constant ($\lambda_z$).

Plasma concentration versus time data for the compounds of interest will be fit individually and simultaneously to appropriate models using nonlinear mixed effects modeling as implemented in NONMEM (version 7.3). Data will be modeled with individual and population approaches. One, two, and three-compartment models incorporating parent and metabolite disposition will be evaluated. First order conditional estimation, Monte Carlo expectation maximization and Monte Carlo Bayesian methods will be explored for estimating the maximum likelihood.

If anti-765IGF antibodies are detected in some or all patients, the effect of the presence of these antibodies on the pharmacokinetic parameters will be investigated. This will be done, for instance, by comparing pharmacokinetic parameters in the first dose, when no anti-drug antibodies could be present, with the parameters in later doses after anti-765IGF antibodies have been shown to have developed, and by comparing the parameters in patients who have anti-765IGF antibodies with those that do not.

7.1.4 Statistical Analysis for Pharmacokinetics

The parameters for 765IGF-MTX, 765IGF, methotrexate, and 7-OH methotrexate will be expressed by descriptive statistics (geometric mean, median, standard deviation and coefficient of variation). The primary pharmacokinetic parameters investigated for each compound will be $AUC_{0-t}$, $AUC_{0-\infty}$, $C_{max}$ and $\lambda_z$. Descriptive statistics will be calculated for the demographic data. Graphs and correlations will be used to examine the distribution of values and bivariate relationships.

7.2 Pharmacodynamic Assessment

Pharmacodynamic samples will be assessed on D1 of cycle 1, D1 and D15 of cycle 2, and D15 of each subsequent cycle.

Systemic responses are defined as plasma concentrations of IGF-1 and blood and serum concentrations of IGF-1R, which will be measured for all subjects and used to assess whether 765IGF-MTX has affected the production of these biological markers. Measures of toxicity (e.g., changes WBC counts, differential cell populations, platelets, etc.) are also considered systemic PD variables.

Pharmacodynamic data will be fit to an appropriate model, using maximum likelihood estimation. To determine whether any relationship exists between systemic activity of drug and biomarkers, the individual baseline corrected maximum biomarker concentrations will be plotted against individual 765IGF-MTX pharmacokinetic values, and Pearson's correlation coefficients will be calculated.

7.3 Evaluation of Potential of 765IGF-MTX for QT Prolongation

QT evaluation will be performed in the PK subjects only during PK collection times by ECG immediately prior to the 765IGF-MTX infusion, 30 minutes after starting the infusion, and at the following time points after completion of the infusion: 60 minutes and 3 hours. In all subjects, QT evaluation will be performed by ECG at baseline (within 14 days of enrollment), at cycle 1 day 1 (before the infusion) and at 30 days (±1 week) after the final dose of 765IGF-MTX.

7.4 Plasma IGF Level and 765IGF-MTX Toxicity/Response

Blood samples from before the infusion on D1 of cycle 1, and before the infusion on D1 and D15 of cycle 2 will be collected from each patient to determine if pre- and during treatment plasma soluble IGF-1 level is associated with 765IGF-MTX toxicity and/or response. Quantification of IGF-1 in plasma will be performed by Quest Diagnostics, test code 16293 by LC/MS. A descriptive analysis will be done between clinical response and marker levels. Please see Appendix VII for biomarker collection procedures.

7.5 Serum and Blood IGF-1R Level and 765IGF-MTX Toxicity/Response

Serum and blood samples from before the infusion on D1 of cycle 1, and before the infusion on D1 and D15 of cycle 2 will be collected from each patient to determine if pre- and within-treatment serum and blood IGF-1R level is associated with 765IGF-MTX toxicity and/or response. Quantification of IGF-1R in plasma will be performed by IGF Oncology using western blotting. A descriptive analysis will be done between clinical response and marker levels. Please see Appendix VII for biomarker collection procedures.

7.6 Formation of Anti-765IG-MTX Antibodies.

Serum samples from before the infusion on D1 of cycle 1, and before the infusion on D1 and D15 of cycle 2 will be collected from each patient and analyzed for anti-drug antibodies by an assay the sponsor has used for detecting anti-765IG-MTX antibodies in preclinical test dogs and rats. The assay is a sandwich ELISA involving plating serum in 96-well plates, adding drug to the wells of the plates to bind to any anti-drug antibodies that may be present in the serum, and then detecting bound 765IGF-MTX drug with an anti-IGF-HRP conjugate antibody from R&D Systems, Quantikine human IGF-1 ELISA kit.

That sandwich assay detects antibodies against 765IGF-MTX. The same assay will be performed where 765IGF protein, instead of 765IGF-MTX is added to the plates. This will detect antibodies against 765IGF protein.

The serum samples will also be analyzed for the presence of neutralizing antibodies. In this assay, serum will be mixed with 765IGF-MTX in an in vitro assay for killing of human MCF7 breast cancer cells to determine whether the addition of patient serum affects the minimum inhibitory concentration of 765IGF-MTX in inhibiting growth of MCF7 cells. This assay will be performed on the same serum samples collected before treatment on Cycle 2, days 1 and 15 and on day 15 of cycles 4 and 6. Please see Appendix VII for biomarker collection procedures.

Risk assessment.

The risk to patients from assaying for anti-765IGF antibodies is minimal and arises only from an additional blood draw before the infusion on D1 of cycle 1, and D1 and D15 of cycle 2. A small amount of blood (7.5 mL/draw) will be taken, which will have no effects on patient health. The risk to patients from possibly developing anti-765IGF antibodies is also small and would be lessened by our knowledge as to whether they are developing these antibodies. First, none of the dogs and none of the rats developed anti-drug antibodies in preclinical testing, so it appears unlikely that patients will develop anti-765IGF antibodies. The risk to patients from developing the antibodies, if it occurs, would be that the antibodies would be expected to possibly reduce the effectiveness of the drug, and would raise a risk of an anaphylactic reaction to administration of the drug. Anaphylactic reactions occur with some biologic medicines, such as Rituximab, and can usually be managed with antihistamines, such as diphenhydramine. Formation of antibodies against 765IGF may also potentially cause similar side effects of antibodies against IGFR1 receptor, such as the possibility of development of hyperglycemia. Monitoring blood sugar levels will be routinely performed in this study.

7.7 Neutralizing Antibodies and 765IGF-MTX Toxicity/Response

Serum samples from before the infusion on D1 of cycle 1 and before the infusion on D1 and D15 of cycle 2, and on D15 of cycles 4 and 6 will be analyzed for the presence of neutralizing antibodies. In this assay, serum will be mixed with 765IGF-MTX in an in vitro assay for killing of human MCF7 breast cancer cells to determine whether the addition of patient serum affects the minimum inhibitory concentration of 765IGF-MTX in inhibiting growth of MCF7 cells. Please see Appendix VII for biomarker collection procedures.

A descriptive analysis will be done correlating neutralizing antibody presence or levels with clinical response to, and toxicity of, 765IGF-MTX.

7.8 IGF-1R Expression Level in Diseased Cells of Bone Marrow Aspirate Via IHC and Flow Cytometry When bone marrow aspirates are collected from patients, a portion will be clotted, fixed, and paraffin embedded; and a second portion will be held at room temperature and shipped overnight the same day. A pathology report will be prepared for the fixed sample. All samples will be held at Mayo Clinic and shipped together at the end of the study with their pathology reports to Quest Diagnostics for IGF-1R expression level testing by IHC with their test code 19429X.

The fresh viable bone marrow aspirate will be shipped overnight the same day to Charles River, Inc., for testing of IGF-1R and CD34 expression by flow cytometry. This assay will be similar to that of He et al.[28]

7.9 IGF-1R Expression Level in Diseased Cells of Whole Blood Via Flow Cytometry Whole blood will be collected in EDTA tubes (6 ml) and shipped overnight the same day in an insulated container at room temperature to Charles River, Inc., for testing of IGF-1R and CD34 expression by flow cytometry. This assay will be similar to that of He et al.[28] This collection and testing will be at baseline and every 8 weeks after treatment is begun.

Results:

To date, 2 subjects have been enrolled, both diagnosed with O-AML. Subject 101 previously had MDS that has transformed to O-AML.

The bone marrow aspirate blast counts and the complete blood counts with differential for both subjects at baseline before treatment and at 8 weeks, after two cycles of treatment (6 doses) are shown in Table 3. Both were dosed at dose level 1 (0.2 microEq/kg). Both were males over 80 years old (80 and 83 years old).

TABLE 3

Bone marrow and hematology results of first two subjects enrolled.

| | Subject | | | | |
|---|---|---|---|---|---|
| | 101 | | 102 | | |
| | Time point | | | | |
| | baseline | 8 week | baseline | 8 weeks | normal range |
| bone marrow parameter | | | | | |
| bone marrow blast percentage | 22 | 5 | 17 | 17 | 0-5 |
| hematology parameters | | | | | |
| Leukocytes × 10(9)/L | 0.8 | 1.8 | 0.8 | 2.9 | 4.5-11 |
| red blood cell count × 10(12)/L | 1.92 | 2.38 | 2.72 | 2.79 | 4.1-5.5 |
| hemoglobin (g/dL) | 7.3 | 8.9 | 9.7 | 9.9 | 12-16 |
| hemotocrit % | 20.5 | 25.4 | 28.1 | 28.5 | 37-47 |
| platelets × 10(9)/L | 12 | 24 | 85 | 39 | 150-450 |
| neutrophils × 10(9)/L | 0.04 | 0.75 | 0.38 | 1.29 | 2-7 |
| lymphocytes × 10(9)/L | 0.71 | 0.87 | 0.38 | 1.40 | 1-3 |
| Monocytes × 10(9)/L | 0.03 | 0.11 | 0.03 | 0.12 | 0.2-1 |
| Eosinophils × 10(9)/L | 0.03 | 0.03 | 0.03 | 0.04 | 0.02-0.5 |

The bone marrow blast cell percentage is the key parameter used to evaluate MDS and the related diseases O-AML, and CMML. It is substantially improved in subject 101 and stable in subject 102. The next key measurement is leukocytes, and that is substantially improved for both subjects. The next important parameters are neutrophils and platelets. Neutrophils are substantially improved for both subjects, and platelets are improved for subject 101 and worse for subject 102. Every blood parameter measured was improved or stable in both subjects except for platelets in subject 102.

The clinical evaluation of both subjects after 8 weeks was stable disease. Stable disease for 8 weeks, with almost all parameters improving, is evidence of efficacy because both of these subjects had an estimated life expectancy when they began treatment of only 3 months, according to the physician principal investigator of the clinical trial.

---

Sequences

SEQ ID NO: 1 MVKGKHHHHHHNGKGKSK

SEQ ID NO: 2 (765IGF)
MVKGKHHHHH HNGKGKSKGP RTLCGAELVD ALQFVCGDRG
FYFNKPTGYG SSSRRAPQTG
IVDECCFRSC DLRRLEMYCA PLKPAKSA

SEQ ID NO: 3 (human IGF-1)
GPETLCGAEL VDALQFVCGD RGFYFNKPTG YGSSSRRAPQ
TGIVDECCFR SCDLRRLEMY
CAPLKPAKSA SEQ ID NO: 4 (IGF132)
FVNQHLCGSHLVEALYL VCGDRG FYFNKPTGYG SSSRRAPQTG
IVDECCFRSCDLRR LEMYCAPLKPAKSA SEQ ID NO: 5 (long-R3-IGF)
MFPAMPLSSLFVN GPRTL CGALVDALQ FVCGDRGFYF
NKPTGYGSSS RRAPQTGIVD ECCFRSCDLR RLEMYCAPLK
PAKSEA SEQ ID NO: 6 (R3-IGF)
GPRTLCGAELVD ALQFVCGDRG FYFNKPTGYG SSSRRAPQTG
IVDECCFRSC DLRRLEMYCA PLKPAKSA SEQ ID NO: 7 des(1-3)IGF1
TLCGAELVD ALQFVCGDRG FYFNKPTGYG SSSRRAPQTG
IVDECCFRSC DLRRLEMYCA PLKPAKSA SEQ ID NO: 8, 403IGF
MTSGHHHHHHSAGVNG FVNQHLCGSHL VEALYLVCGD RGFYFNKPTG
YGSSSRRAPQ TGIVDECCFR SCDLRRLEMY CAPLKPAKSA SEQ ID NO: 9, 784IGF
MVKQIESKTAFQEALDAAGDKLVVVDFSATWCGHCKMIKPFFHSLSEKYS
NVIFLEVDVDDSQDVASESEVKSMPTFQFFKKGQKVGEFSGANKEKLEAT
INELVGSKSGHHHHHH
SAKGGPRTLCGAELVDALQFVCGDRGFYFNKFTGYGSSSRRAPQTGIVDE
CCFRSCDLRR
LEMYCAPLKPAKSA SEQ ID NO: 10, 785IGF
MVKQIESKTAFQEALDAAGDKLVVVDFSATWCGHCKMIKPFFHSLSEKYS
NVIFLEVDVDDSQDVASESEVKSMPTFQFFKKGQKVGEFSGANKEKLEAT
INELVGSKSGHHHHHH
SAKGFVNQHLCGSHLVEALYLVCGDRGFYFNKFTGYGSSSRRAPQTGIVD
ECCFRSCDLR
RLEMYCAPLKPAKSA SEQ ID NO: 11, 764IGF
MVKGKHHHHHHNGKGKSKFVNQHLCGSHLVEALYLVCGDRGFYFNKPTGY
GSSSRRAPQTGIVDECCFRSCDLRRLEMYCAPLKPAKSA All patents, patent documents, and other references cited are incorporated by reference.

What is claimed is:

1. A method of treating a patient for myelodysplastic syndrome (MDS), oligoblastic acute myelogenous leukemia (O-AML), or chronic myelomonocytic leukemia (CMML) comprising:
 administering to a patient in recognized need of treatment for MDS, O-AML, or CMML an agent comprising:
 an insulin-like growth factor type 1 receptor (IGF-1R) ligand conjugated to an anti-cancer chemotherapy drug;
 wherein the IGF-1R ligand is covalently attached to the anti-cancer chemotherapy drug;
 wherein the IGF-1R ligand is a variant of IGF-1 that has reduced binding affinity for IGF-1 binding proteins as compared to IGF-1; and
 wherein the IGF-1R ligand is not IGF-1 (SEQ ID NO:3) and is or comprises 765IGF (SEQ ID NO:2), IGF132 (SEQ ID NO:4), long-R3-IGF (SEQ ID NO:5), R3-IGF (SEQ ID NO:6), or des(1-3)-IGF (SEQ ID NO:7), or a variant at least 90% identical to IGF-1 (SEQ ID NO:3);
 wherein the anti-cancer chemotherapy drug is methotrexate and is covalently attached to the IGF-1R ligand, wherein the agent is administered by infusion dissolved in a volume of 100 ml to 1 liter of 5% to 10% dextrose in water at a dose of 0.2 to 2.5 microEq/kg patient body weight;
 wherein the treating inhibits growth of cancer cells.

2. The method of claim 1 wherein the method is a method of treating a patient for MDS and the patient is in recognized need of treatment for MDS.

3. The method of claim 1 wherein the agent is 765IGF-MTX.

4. The method of claim 1 wherein the method comprises dosing the patient with the agent once or twice per week for at least 3 weeks.

5. A method of treating a patient for a cancer that is acute myeloid leukemia (AML), chronic myeloid leukemia (CML), O-AML, CMML, or MDS comprising:
 administering to a patient in recognized need of treatment for AML, CML, O-AML, CMML, or MDS (a) a hypomethylating agent and (b) an agent comprising:
 an insulin-like growth factor type 1 receptor (IGF-1R) ligand conjugated to methotrexate;
 wherein the IGF-1R ligand is covalently attached to the methotrexate;
 wherein the IGF-1R ligand is a variant of IGF-1 that has reduced binding affinity for IGF-1 binding proteins as compared to IGF-1; and
 wherein the IGF-1R ligand is not IGF-1 (SEQ ID NO:3) and is or comprises 765IGF (SEQ ID NO:2), IGF132 (SEQ ID NO:4), long-R3-IGF (SEQ ID NO:5), R3-IGF (SEQ ID NO:6), or des(1-3)-IGF (SEQ ID NO:7), or a variant at least 90% identical to IGF-1 (SEQ ID NO:3);
 wherein the agent (b) is administered by infusion dissolved in a volume of 100 ml to 1 liter of 5% to 10% dextrose in water at a dose of 0.2 to 2.5 microEq/kg patient body weight;
 wherein the treating inhibits growth of cancer cells.

6. The method of claim 5 wherein the method is a method of treating a patient for MDS, O-AML, or CMML, and the patient is in recognized need for treatment of MDS, O-AML, or CMML.

7. The method of claim 5 wherein the hypomethylating agent is azacitidine.

8. The method of claim 5 wherein the agent (b) is 765IGF-MTX.

9. The method of claim 5 wherein the method comprises treating the patient with azacitidine and the agent (b) is 765IGF-MTX.

* * * * *

SEQUENCE LISTING

<160> NUMBER OF SEQ ID NOS: 11

<210> SEQ ID NO 1
<211> LENGTH: 18
<212> TYPE: PRT
<213> ORGANISM: Artificial
<220> FEATURE:
<223> OTHER INFORMATION: Synthesized

<400> SEQUENCE: 1

Met Val Lys Gly Lys His His His His His Asn Gly Lys Gly Lys
1               5                   10                  15

Ser Lys

<210> SEQ ID NO 2
<211> LENGTH: 88
<212> TYPE: PRT
<213> ORGANISM: Artificial
<220> FEATURE:
<223> OTHER INFORMATION: Synthesized

<400> SEQUENCE: 2

Met Val Lys Gly Lys His His His His His Asn Gly Lys Gly Lys
1               5                   10                  15

Ser Lys Gly Pro Arg Thr Leu Cys Gly Ala Glu Leu Val Asp Ala Leu
            20                  25                  30

Gln Phe Val Cys Gly Asp Arg Gly Phe Tyr Phe Asn Lys Pro Thr Gly
        35                  40                  45

Tyr Gly Ser Ser Ser Arg Arg Ala Pro Gln Thr Gly Ile Val Asp Glu
    50                  55                  60

Cys Cys Phe Arg Ser Cys Asp Leu Arg Arg Leu Glu Met Tyr Cys Ala
65                  70                  75                  80

Pro Leu Lys Pro Ala Lys Ser Ala
                85

<210> SEQ ID NO 3
<211> LENGTH: 70
<212> TYPE: PRT
<213> ORGANISM: Homo sapiens

<400> SEQUENCE: 3

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70

<210> SEQ ID NO 4
<211> LENGTH: 71
<212> TYPE: PRT
<213> ORGANISM: Artificial
<220> FEATURE:
<223> OTHER INFORMATION: Synthesized

<400> SEQUENCE: 4

Phe Val Asn Gln His Leu Cys Gly Ser His Leu Val Glu Ala Leu Tyr

```
                1               5                  10                  15
Leu Val Cys Gly Asp Arg Gly Phe Tyr Phe Asn Lys Pro Thr Gly Tyr
                20                  25                  30

Gly Ser Ser Ser Arg Arg Ala Pro Gln Thr Gly Ile Val Asp Glu Cys
            35                  40                  45

Cys Phe Arg Ser Cys Asp Leu Arg Arg Leu Glu Met Tyr Cys Ala Pro
        50                  55                  60

Leu Lys Pro Ala Lys Ser Ala
65                  70

<210> SEQ ID NO 5
<211> LENGTH: 83
<212> TYPE: PRT
<213> ORGANISM: Artificial
<220> FEATURE:
<223> OTHER INFORMATION: Synthesized

<400> SEQUENCE: 5

Met Phe Pro Ala Met Pro Leu Ser Ser Leu Phe Val Asn Gly Pro Arg
1               5                   10                  15

Thr Leu Cys Gly Ala Leu Val Asp Ala Leu Gln Phe Val Cys Gly Asp
                20                  25                  30

Arg Gly Phe Tyr Phe Asn Lys Pro Thr Gly Tyr Gly Ser Ser Ser Arg
            35                  40                  45

Arg Ala Pro Gln Thr Gly Ile Val Asp Glu Cys Cys Phe Arg Ser Cys
        50                  55                  60

Asp Leu Arg Arg Leu Glu Met Tyr Cys Ala Pro Leu Lys Pro Ala Lys
65                  70                  75                  80

Ser Glu Ala

<210> SEQ ID NO 6
<211> LENGTH: 70
<212> TYPE: PRT
<213> ORGANISM: Artificial
<220> FEATURE:
<223> OTHER INFORMATION: Synthesized

<400> SEQUENCE: 6

Gly Pro Arg Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
        50                  55                  60

Lys Pro Ala Lys Ser Ala
65                  70

<210> SEQ ID NO 7
<211> LENGTH: 67
<212> TYPE: PRT
<213> ORGANISM: Artificial
<220> FEATURE:
<223> OTHER INFORMATION: Synthesized

<400> SEQUENCE: 7

Thr Leu Cys Gly Ala Glu Leu Val Asp Ala Leu Gln Phe Val Cys Gly
1               5                   10                  15
```

```
Asp Arg Gly Phe Tyr Phe Asn Lys Pro Thr Gly Tyr Gly Ser Ser
            20                  25                  30

Arg Arg Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
50                  55                  60

Lys Ser Ala
65

<210> SEQ ID NO 8
<211> LENGTH: 87
<212> TYPE: PRT
<213> ORGANISM: Artificial
<220> FEATURE:
<223> OTHER INFORMATION: Synthesized

<400> SEQUENCE: 8

Met Thr Ser Gly His His His His His His Ser Ala Gly Val Asn Gly
1               5                   10                  15

Phe Val Asn Gln His Leu Cys Gly Ser His Leu Val Glu Ala Leu Tyr
            20                  25                  30

Leu Val Cys Gly Asp Arg Gly Phe Tyr Phe Asn Lys Pro Thr Gly Tyr
        35                  40                  45

Gly Ser Ser Ser Arg Arg Ala Pro Gln Thr Gly Ile Val Asp Glu Cys
    50                  55                  60

Cys Phe Arg Ser Cys Asp Leu Arg Arg Leu Glu Met Tyr Cys Ala Pro
65                  70                  75                  80

Leu Lys Pro Ala Lys Ser Ala
                85

<210> SEQ ID NO 9
<211> LENGTH: 190
<212> TYPE: PRT
<213> ORGANISM: Artificial
<220> FEATURE:
<223> OTHER INFORMATION: Synthesized

<400> SEQUENCE: 9

Met Val Lys Gln Ile Glu Ser Lys Thr Ala Phe Gln Glu Ala Leu Asp
1               5                   10                  15

Ala Ala Gly Asp Lys Leu Val Val Val Asp Phe Ser Ala Thr Trp Cys
            20                  25                  30

Gly His Cys Lys Met Ile Lys Pro Phe Phe His Ser Leu Ser Glu Lys
        35                  40                  45

Tyr Ser Asn Val Ile Phe Leu Glu Val Asp Val Asp Asp Ser Gln Asp
    50                  55                  60

Val Ala Ser Glu Ser Glu Val Lys Ser Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val Gly Ser Lys Ser Gly His His
            100                 105                 110

His His His His Ser Ala Lys Gly Gly Pro Arg Thr Leu Cys Gly Ala
        115                 120                 125

Glu Leu Val Asp Ala Leu Gln Phe Val Cys Gly Asp Arg Gly Phe Tyr
    130                 135                 140

Phe Asn Lys Pro Thr Gly Tyr Gly Ser Ser Ser Arg Arg Ala Pro Gln
145                 150                 155                 160
```

```
Thr Gly Ile Val Asp Glu Cys Cys Phe Arg Ser Cys Asp Leu Arg Arg
            165                 170                 175

Leu Glu Met Tyr Cys Ala Pro Leu Lys Pro Ala Lys Ser Ala
        180                 185                 190

<210> SEQ ID NO 10
<211> LENGTH: 191
<212> TYPE: PRT
<213> ORGANISM: Artificial
<220> FEATURE:
<223> OTHER INFORMATION: Synthesized

<400> SEQUENCE: 10

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
            20                  25                  30      Cys

Gly His Cys Lys Met Ile Lys Pro Phe Phe His Ser Leu Ser Glu Lys
        35                  40                  45

Tyr Ser Asn Val Ile Phe Leu Glu Val Asp Val Asp Ser Gln Asp
    50                  55                  60              Asp

Val Ala Ser Glu Ser Glu Val Lys Ser Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val Gly Ser Lys Ser Gly His His
            100                 105                 110

His His His His Ser Ala Lys Gly Phe Val Asn Gln His Leu Cys Gly
        115                 120                 125

Ser His Leu Val Glu Ala Leu Tyr Leu Val Cys Gly Asp Arg Gly Phe
    130                 135                 140

Tyr Phe Asn Lys Pro Thr Gly Tyr Gly Ser Ser Ser Arg Arg Ala Pro
145                 150                 155                 160

Gln Thr Gly Ile Val Asp Glu Cys Cys Phe Arg Ser Cys Asp Leu Arg
                165                 170                 175

Arg Leu Glu Met Tyr Cys Ala Pro Leu Lys Pro Ala Lys Ser Ala
            180                 185                 190

<210> SEQ ID NO 11
<211> LENGTH: 89
<212> TYPE: PRT
<213> ORGANISM: Artificial
<220> FEATURE:
<223> OTHER INFORMATION: Synthesized

<400> SEQUENCE: 11

Met Val Lys Gly Lys His His His His His Asn Gly Lys Gly Lys
1               5                   10                  15

Ser Lys Phe Val Asn Gln His Leu Cys Gly Ser His Leu Val Glu Ala
            20                  25                  30

Leu Tyr Leu Val Cys Gly Asp Arg Gly Phe Tyr Phe Asn Lys Pro Thr
        35                  40                  45

Gly Tyr Gly Ser Ser Ser Arg Arg Ala Pro Gln Thr Gly Ile Val Asp
    50                  55                  60
```

```
Glu Cys Cys Phe Arg Ser Cys Asp Leu Arg Arg Leu Glu Met Tyr Cys
65                  70                  75                  80
Ala Pro Leu Lys Pro Ala Lys Ser Ala
                85
```